(12) United States Patent
Jang et al.

(10) Patent No.: US 11,992,394 B2
(45) Date of Patent: *May 28, 2024

(54) ABSORBENT ARTICLE WITH SELECTIVELY POSITIONED WAIST CONTAINMENT MEMBER HAVING AN IMPROVED WAIST SEAL

(71) Applicant: Kimberly-Clark Worldwide, Inc., Neenah, WI (US)

(72) Inventors: KyungSik Jang, Daejeon (KR); Nickolas Barnes, Menasha, WI (US); Roxanne M. Zuleger, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 1239 days.

This patent is subject to a terminal disclaimer.

(21) Appl. No.: 16/597,320

(22) Filed: Oct. 9, 2019

(65) Prior Publication Data

US 2020/0038256 A1 Feb. 6, 2020

Related U.S. Application Data

(62) Division of application No. 15/307,932, filed as application No. PCT/US2015/052894 on Sep. 29, 2015, now Pat. No. 10,470,943.

(51) Int. Cl.
*A61F 13/15* (2006.01)
*A61F 13/49* (2006.01)
(Continued)

(52) U.S. Cl.
CPC ...... *A61F 13/495* (2013.01); *A61F 13/49001* (2013.01); *A61F 13/49011* (2013.01);
(Continued)

(58) Field of Classification Search
CPC .......... A61F 13/49001; A61F 13/49011; A61F 13/49012; A61F 13/4902; A61F 13/49466;
(Continued)

(56) References Cited

U.S. PATENT DOCUMENTS 3,395,708 A 8/1968 Laurence et al.
3,800,796 A 4/1974 Jacob
(Continued)

FOREIGN PATENT DOCUMENTS

CN 1200662 A 12/1998
CN 1853592 A 11/2006
(Continued)

*Primary Examiner* — Bradley H Philips
(74) *Attorney, Agent, or Firm* — KIMBERLY-CLARK WORLDWIDE, INC.

(57) ABSTRACT

An absorbent article can include a chassis including an absorbent body. The chassis can include a body facing surface. The absorbent article can also include a waist containment member. The waist containment member can include a proximal portion coupled to the body facing surface of the chassis and a distal portion that includes a distal edge. The proximal portion includes proximal portion elastic members and the distal portion can include distal portion elastic members. The distal portion can be free to move with respect to the chassis when the absorbent article is in a relaxed configuration.

13 Claims, 12 Drawing Sheets

(51) Int. Cl.
*A61F 13/494* (2006.01)
*A61F 13/495* (2006.01)

(52) U.S. Cl.
CPC .... *A61F 13/49012* (2013.01); *A61F 13/4902* (2013.01); *A61F 13/49466* (2013.01); *A61F 13/49473* (2013.01); *A61F 2013/49025* (2013.01); *A61F 2013/49092* (2013.01)

(58) Field of Classification Search
CPC .............. A61F 13/49473; A61F 13/495; A61F 2013/49025; A61F 2013/49092
See application file for complete search history.

(56) References Cited

U.S. PATENT DOCUMENTS

| | | |
|---|---|---|
| 3,848,594 A | 11/1974 | Buell |
| 3,860,003 A | 1/1975 | Buell |
| 3,930,501 A | 1/1976 | Schaar |
| 3,978,861 A | 9/1976 | Schaar |
| 3,995,640 A | 12/1976 | Schaar |
| 4,074,716 A | 2/1978 | Schaar |
| 4,525,407 A | 6/1985 | Ness |
| 4,642,110 A | 2/1987 | Dudek |
| 4,643,729 A | 2/1987 | Laplanche |
| 4,657,539 A | 4/1987 | Hasse |
| 4,657,802 A | 4/1987 | Morman |
| 4,681,579 A | 7/1987 | Toussant et al. |
| 4,735,624 A | 4/1988 | Mazars |
| 4,738,677 A | 4/1988 | Foreman |
| 4,741,949 A | 5/1988 | Morman et al. |
| 4,753,646 A | 6/1988 | Enloe |
| 4,808,176 A | 2/1989 | Kielpikowski |
| 4,808,177 A | 2/1989 | DesMarais et al. |
| 4,822,435 A | 4/1989 | Igaue et al. |
| 4,850,990 A | 7/1989 | Huntoon et al. |
| 4,935,021 A | 6/1990 | Huffman et al. |
| 4,938,755 A | 7/1990 | Foreman |
| 4,977,011 A | 12/1990 | Smith |
| 5,026,364 A | 6/1991 | Robertson |
| 5,064,421 A | 11/1991 | Tracy |
| 5,069,672 A | 12/1991 | Wippler et al. |
| 5,106,385 A | 4/1992 | Allen et al. |
| 5,151,091 A | 9/1992 | Glaug et al. |
| 5,151,092 A | 9/1992 | Buell et al. |
| 5,187,817 A | 2/1993 | Zolner |
| 5,209,801 A | 5/1993 | Smith |
| 5,366,452 A | 11/1994 | Widlund et al. |
| 5,397,318 A | 3/1995 | Dreier |
| 5,413,570 A | 5/1995 | Enloe |
| 5,439,459 A | 8/1995 | Tanji et al. |
| 5,451,219 A | 9/1995 | Suzuki et al. |
| 5,514,104 A | 5/1996 | Cole et al. |
| 5,514,121 A | 5/1996 | Roe et al. |
| 5,531,730 A | 7/1996 | Dreier |
| 5,540,671 A | 7/1996 | Dreier |
| 5,558,660 A | 9/1996 | Dreier |
| 5,558,661 A | 9/1996 | Roe et al. |
| 5,569,227 A | 10/1996 | Vandemoortele et al. |
| 5,582,606 A | 12/1996 | Bruemmer et al. |
| 5,593,401 A | 1/1997 | Sosalla et al. |
| 5,624,422 A | 4/1997 | Allen |
| 5,643,242 A | 7/1997 | Lavon et al. |
| 5,649,918 A | 7/1997 | Schleinz |
| 5,667,503 A | 9/1997 | Roe et al. |
| 5,672,166 A | 9/1997 | Vandemoortele |
| 5,674,215 A | 10/1997 | Ronnberg |
| 5,685,873 A | 11/1997 | Bruemmer |
| 5,690,627 A | 11/1997 | Clear et al. |
| 5,695,488 A | 12/1997 | Sosalla |
| 5,776,121 A | 7/1998 | Roe et al. |
| 5,795,347 A | 8/1998 | Roe et al. |
| 5,817,086 A | 10/1998 | Kling |
| 5,827,259 A | 10/1998 | Laux et al. |
| 5,858,012 A | 1/1999 | Yamaki et al. |
| 5,895,382 A | 4/1999 | Popp et al. |
| 5,904,675 A | 5/1999 | Laux et al. |
| 5,931,826 A | 8/1999 | Faulks et al. |
| 5,938,652 A | 8/1999 | Sauer |
| 5,993,433 A | 11/1999 | St. Louis et al. |
| 6,103,952 A | 8/2000 | Coles et al. |
| 6,132,410 A | 10/2000 | Van Gompel et al. |
| 6,135,988 A | 10/2000 | Turner et al. |
| 6,142,985 A | 11/2000 | Feist |
| 6,149,638 A | 11/2000 | Vogt et al. |
| 6,174,303 B1 | 1/2001 | Suprise et al. |
| 6,217,563 B1 | 4/2001 | Van Gompel et al. |
| 6,258,076 B1 | 7/2001 | Glaug et al. |
| 6,264,639 B1 | 7/2001 | Sauer |
| 6,264,641 B1 | 7/2001 | Van Gompel et al. |
| 6,280,426 B1 | 8/2001 | Turner et al. |
| 6,293,937 B2 | 9/2001 | Matsushita et al. |
| 6,306,122 B1 | 10/2001 | Narawa et al. |
| 6,315,764 B1 | 11/2001 | Faulks et al. |
| 6,425,889 B1 * | 7/2002 | Kitaoka ............ A61F 13/49466 604/385.19 |
| 6,443,933 B1 | 9/2002 | Suzuki et al. |
| 6,455,753 B1 | 9/2002 | Glaug et al. |
| 6,458,114 B1 | 10/2002 | Mishima et al. |
| 6,482,194 B1 | 11/2002 | Putzer |
| 6,491,677 B1 | 12/2002 | Glaug et al. |
| 6,494,872 B1 | 12/2002 | Suzuki et al. |
| 6,506,185 B1 | 1/2003 | Sauer et al. |
| 6,527,756 B1 | 3/2003 | Mishima et al. |
| 6,638,262 B2 | 10/2003 | Suzuki et al. |
| 6,648,870 B2 | 11/2003 | Itoh et al. |
| 6,699,228 B1 | 3/2004 | Chmielewski et al. |
| 6,827,806 B2 | 12/2004 | Uitenbroek et al. |
| 6,838,591 B2 | 1/2005 | Waksmundzki et al. |
| 6,881,207 B1 | 4/2005 | Tracy |
| 6,890,327 B2 | 5/2005 | Suzuki et al. |
| 7,066,921 B2 | 6/2006 | Schmoker et al. |
| 7,166,093 B2 | 1/2007 | Drevik et al. |
| 7,166,095 B1 | 1/2007 | Coates |
| 7,247,152 B2 | 7/2007 | Klemp et al. |
| 7,604,625 B2 | 10/2009 | Turi et al. |
| 7,666,173 B2 | 2/2010 | Mishima et al. |
| 7,767,876 B2 | 8/2010 | Davis et al. |
| 7,842,021 B2 | 11/2010 | Wood et al. |
| 7,879,017 B1 | 2/2011 | Tabata et al. |
| 7,993,314 B2 | 8/2011 | Asp et al. |
| 8,075,543 B2 | 12/2011 | Okuda |
| 9,044,359 B2 | 6/2015 | Wciorka et al. |
| 10,010,458 B2 | 7/2018 | Barnes |
| 10,159,610 B2 | 12/2018 | Barnes |
| 2001/0016720 A1 | 8/2001 | Otsubo |
| 2002/0045878 A1 | 4/2002 | Shimoe et al. |
| 2002/0082570 A1 | 6/2002 | Mishima et al. |
| 2002/0147438 A1 | 10/2002 | Tanaka et al. |
| 2003/0045853 A1 | 3/2003 | Sauer |
| 2003/0050616 A1 | 3/2003 | Reynolds et al. |
| 2003/0109844 A1 | 6/2003 | Gibbs |
| 2003/0119405 A1 | 6/2003 | Abuto et al. |
| 2003/0216705 A1 * | 11/2003 | Coates .................. A61F 13/495 604/386 |
| 2004/0002690 A1 | 1/2004 | Miyamoto |
| 2004/0019343 A1 | 1/2004 | Olson et al. |
| 2004/0127882 A1 | 7/2004 | Weber |
| 2004/0243086 A1 | 12/2004 | VanGompel et al. |
| 2005/0027274 A1 | 2/2005 | Suzuki et al. |
| 2005/0148974 A1 | 7/2005 | Datta et al. |
| 2005/0215974 A1 | 9/2005 | Susan |
| 2005/0256488 A1 | 11/2005 | Sperl |
| 2006/0058738 A1 | 3/2006 | Ponzi et al. |
| 2006/0058767 A1 | 3/2006 | Zhang et al. |
| 2007/0093164 A1 | 4/2007 | Nakaoka |
| 2007/0112322 A1 | 5/2007 | Ashton et al. |
| 2007/0255245 A1 | 11/2007 | Asp et al. |
| 2007/0293832 A1 | 12/2007 | Wood et al. |
| 2008/0300560 A1 | 12/2008 | Magnusson et al. |
| 2010/0305533 A1 | 12/2010 | Ashton et al. |
| 2012/0277703 A1 | 11/2012 | Rhein et al. |
| 2012/0323207 A1 | 12/2012 | Takaishi |
| 2013/0012905 A1 | 1/2013 | Katsuragawa et al. |

(56) References Cited

U.S. PATENT DOCUMENTS

| | | | |
|---|---|---|---|
| 2013/0012906 A1 | 1/2013 | Takino | |
| 2013/0012907 A1 | 1/2013 | Sasayama et al. | |
| 2013/0046266 A1 | 2/2013 | Kawakami | |
| 2014/0018761 A1 | 1/2014 | Orchard, IV et al. | |
| 2014/0121623 A1 | 5/2014 | Kirby et al. | |
| 2014/0128829 A1 | 5/2014 | Miyake et al. | |
| 2014/0257231 A1 | 9/2014 | Wang et al. | |
| 2014/0350504 A1 | 11/2014 | Popp et al. | |
| 2015/0051568 A1 | 2/2015 | Sakaguchi et al. | |
| 2015/0182388 A1 | 7/2015 | Katsuragawa et al. | |
| 2017/0000658 A1* | 1/2017 | Chatterjee | A61F 13/49 |
| 2017/0128281 A1* | 5/2017 | Takino | A61F 13/495 |
| 2017/0239104 A1 | 8/2017 | Jang et al. | |
| 2017/0246054 A1 | 8/2017 | Bishop et al. | |
| 2017/0296401 A1 | 10/2017 | Sugiyama et al. | |
| 2018/0055698 A1 | 3/2018 | Bishop et al. | |
| 2018/0071155 A1 | 3/2018 | Bishop et al. | |
| 2018/0104116 A1 | 4/2018 | Bishop et al. | |
| 2019/0083331 A1 | 3/2019 | Barnes | |

FOREIGN PATENT DOCUMENTS

| | | |
|---|---|---|
| CN | 102065811 A | 5/2011 |
| CN | 102065813 B | 11/2014 |
| CN | 204072501 U | 1/2015 |
| JP | 2001178772 A | 7/2001 |
| JP | 4754634 B2 | 8/2011 |
| KR | 100648562 B1 | 11/2006 |
| KR | 2020130001181 U | 2/2013 |
| WO | 9601607 A1 | 1/1996 |
| WO | 0037008 A1 | 6/2000 |
| WO | 2013021897 A1 | 2/2013 |
| WO | 2016159983 A1 | 10/2016 |

* cited by examiner

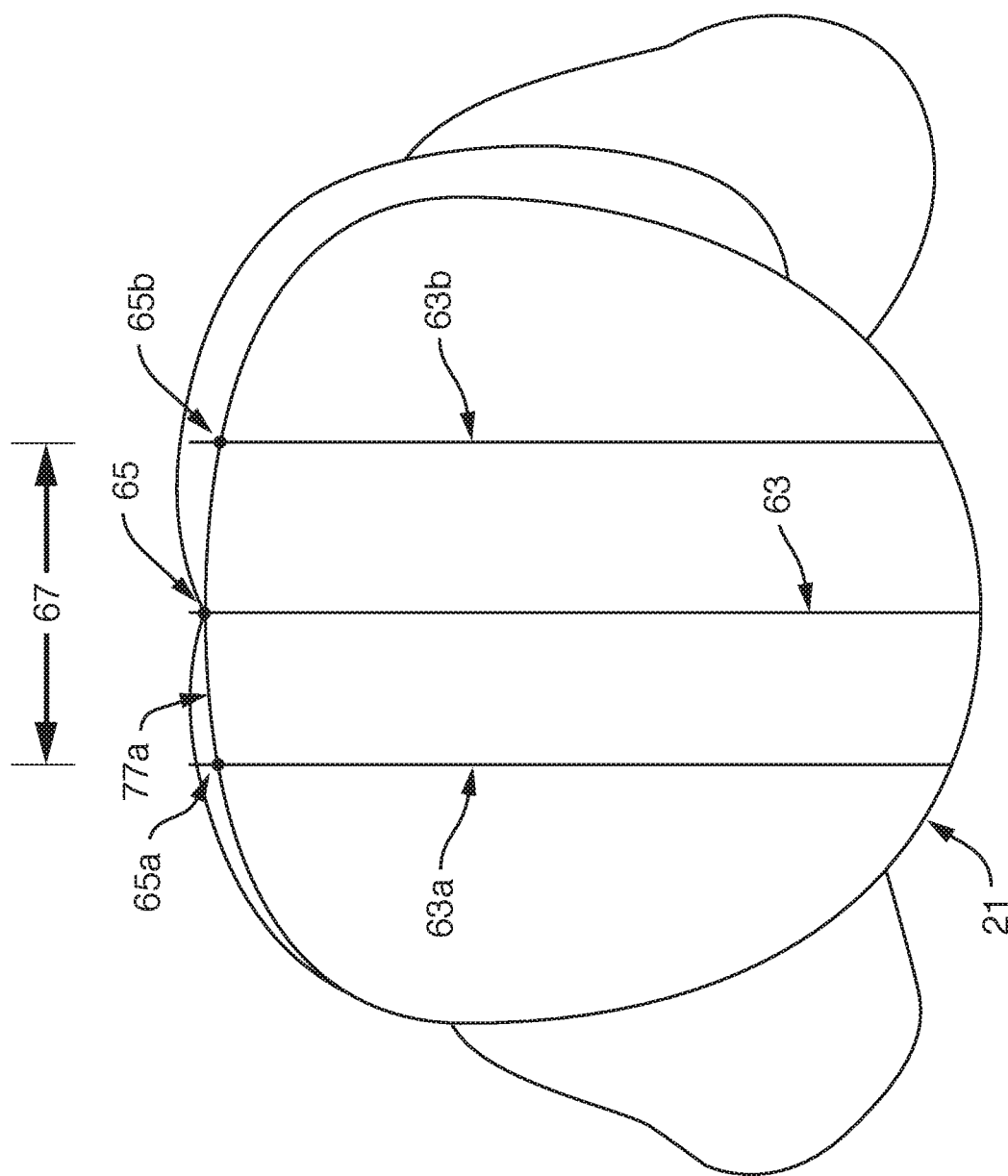

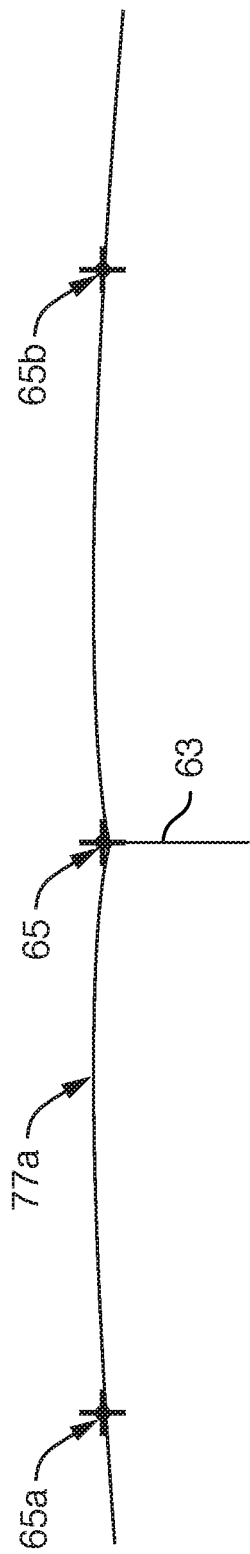
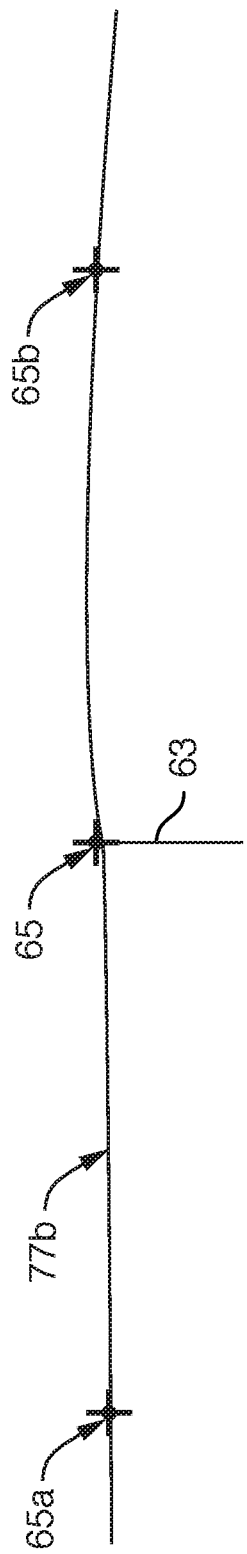

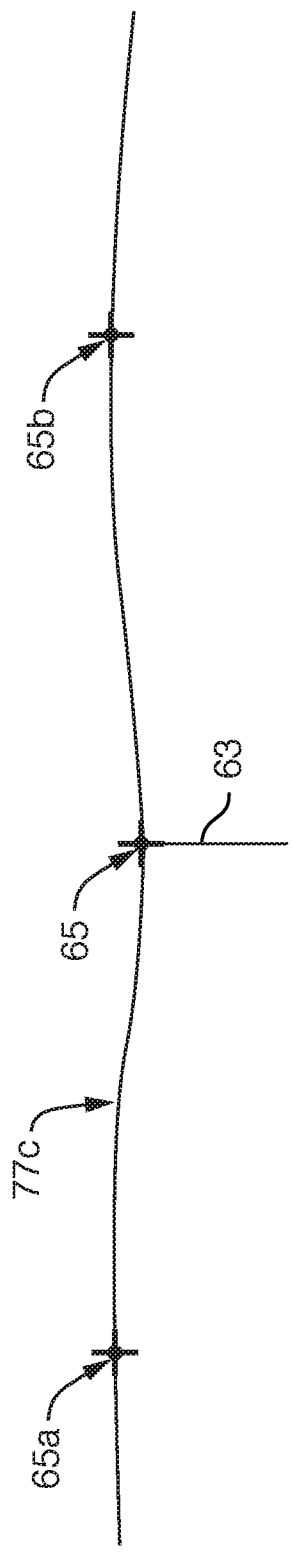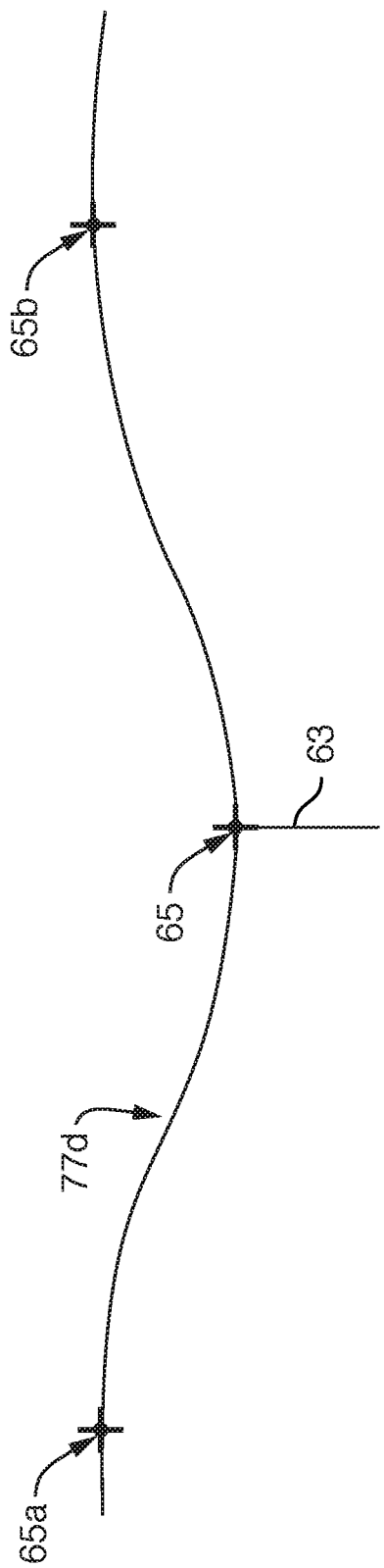

ABSORBENT ARTICLE WITH SELECTIVELY POSITIONED WAIST CONTAINMENT MEMBER HAVING AN IMPROVED WAIST SEAL

CROSS-REFERENCE TO RELATED APPLICATIONS

The present application is a continuation application and claims priority to U.S. patent application Ser. No. 15/307,932, filed Oct. 31, 2016, which is the National Stage of International Application No. PCT/US2015/52894, filed Sep. 29, 2015.

TECHNICAL FIELD

The present disclosure relates to absorbent articles.

BACKGROUND OF THE DISCLOSURE

A primary function of personal care absorbent articles is to absorb and retain body exudates such as urine, fecal material, blood, and menses with additional desired attributes including low leakage of the exudates from the absorbent article and a dry feel to the wearer of the absorbent article. By preventing leakage of the exudates from the absorbent article, the absorbent article intends to prevent the body exudates from soiling or contaminating a wearer's or caregiver's clothing or other articles, such as bedding, that can come in contact with the wearer.

One common mode of failure is for exudates to leak out of the rear waist region or the front waist region of an absorbent article. As one example, fecal material that is not absorbed or contained by the absorbent article can move past the gaps between the absorbent article and the wearer's skin in the rear waist region and soil or contaminate the wearer's skin and clothing near their back. This may be more common of an occurrence for semi-solid fecal material, such as low viscosity fecal material, which can be prevalent with younger children. Such exudates can move around on the bodyside liner of an absorbent article under the influence of gravity, motion, and pressure by the wearer of the absorbent article. In such a circumstance, not only does the wearer's absorbent article need to be changed, but the wearer's clothing and/or bedding often also needs to be changed, resulting in additional work, expense, and stress for the caregiver.

Attempts have been made in the past to provide containment systems, especially on the bodyside liner or near the rear waist region to solve the problems described above. One example is by providing a waist elastic member and not adhering to the bodyside liner a portion of the waist containment member closest to the lateral axis of the absorbent article to the bodyside liner, such that the non-adhered portion of the waist elastic member can provide a containment pocket for exudates. One example of this configuration is a HUGGIES® Little Snugglers diaper. Although absorbent articles with such containment members intend to prevent leakage of exudates and have functioned adequately, failures can still occur.

One such problem relates to the waist elastic tension of the waistband area. In some designs, the tensioning automatically causes the fasteners to be pulled in towards the longitudinal centerline of the product which in turn makes it more difficult to lay the diaper in an open, flat configuration for donning purposes. A second problem is that some designs may pose an aesthetic fault when viewing the back of the absorbent article when being worn. The waist region will not have elasticity high enough up the back of the product, allowing the back edge to pull away from the user's skin resulting in the formation of a gap. This action may make the product appear too lose, when in reality, it is not.

Thus, there is a desire for improvements to containment systems and containment members of absorbent articles to prevent leakage of exudates, especially in the waist regions of the absorbent article. There is also a desire for improvements in containment systems to have increased void volumes to hold body exudates until the absorbent article can be changed.

SUMMARY OF THE DISCLOSURE

In one embodiment absorbent article can include a front waist region including a front waist edge, a rear waist region including a rear waist edge with a crotch region disposed intermediate the front waist edge and the rear waist edge. The absorbent article defines a longitudinal axis, a lateral axis located midway between the front waist edge and the rear waist edge and a vertical axis. The absorbent article has a chassis including an absorbent body with the chassis including a body facing surface. The absorbent article has a waist containment member disposed on the body facing surface of the chassis with the waist containment member comprising a waist containment material having a first longitudinal side edge and a second longitudinal side edge, a first end edge and a second end edge. The waist containment member has a proximal portion with a proximal edge and including a proximal portion elastic member with the proximal portion being coupled to the body facing surface of the chassis adjacent the front waist edge or the rear waist edge. The waist containment member also has a distal portion with a distal edge and the waist containment material has a first fold extending in the direction of the lateral axis. The first fold is closer than the proximal portion elastic member to the respective front waist edge or rear waist edge to which the proximal portion is more closely coupled when the absorbent article is in a stretched, laid flat configuration. The distal edge is closer to lateral axis than the first fold and the distal portion is free to move with respect to the chassis when the absorbent article is in a relaxed configuration so as to form a pocket with the chassis.

In an alternate embodiment, an absorbent article includes a front waist region including a front waist edge, a rear waist region including a rear waist edge with a crotch region disposed intermediate the front waist edge and the rear waist edge. The absorbent article defines a longitudinal axis, a lateral axis located midway between the front waist edge and the rear waist edge and a vertical axis. The absorbent article has a chassis including an absorbent body with the chassis including a body facing surface. A waist containment member is disposed on the body facing surface of the chassis with the waist containment member having a first longitudinal side edge and a second longitudinal side edge, a first end edge and a second end edge. The waist containment member has a proximal portion with a proximal edge defining a proximal portion lateral width between the first longitudinal side edge and the second longitudinal side edge in the proximal portion. The waist containment member includes a proximal portion elastic member with the proximal portion being coupled to the body facing surface of the chassis adjacent the front waist edge or the rear waist edge. The waist containment member has a distal portion with a distal edge defining a distal portion lateral width between the first longitudinal side edge and the second longitudinal side edge in the distal portion. The proximal portion lateral width is equal to or greater than the distal portion lateral width when the absorbent article is in a stretched, laid flat configuration. Further, the distal edge is free to move with respect to the chassis when the absorbent article is in a relaxed configuration so as to form a pocket with the chassis.

BRIEF DESCRIPTION OF DRAWINGS

A full and enabling disclosure thereof, directed to one of ordinary skill in the art, is set forth more particularly in the remainder of the specification, which makes reference to the appended figures in which:

FIG. 7 is a top view of the torso of FIG. 6.

FIG. 8A is a profile of the back region of the torso of FIG. 5 viewed from a top plan view, with the profile being taken at the waistline as shown in FIG. 7.

FIG. 8B is a profile of the back region of the torso of FIG. 5 viewed from a top plan view, with the profile being taken 25 millimeters below the waistline.

FIG. 8C is a profile of the back region of the torso of FIG. 5 viewed from a top plan view, with the profile being taken 50 millimeters below the waistline.

FIG. 8D is a profile of the back region of the torso of FIG. 5 viewed from a top plan view, with the profile being taken 75 millimeters below the waistline.

Figure 1:
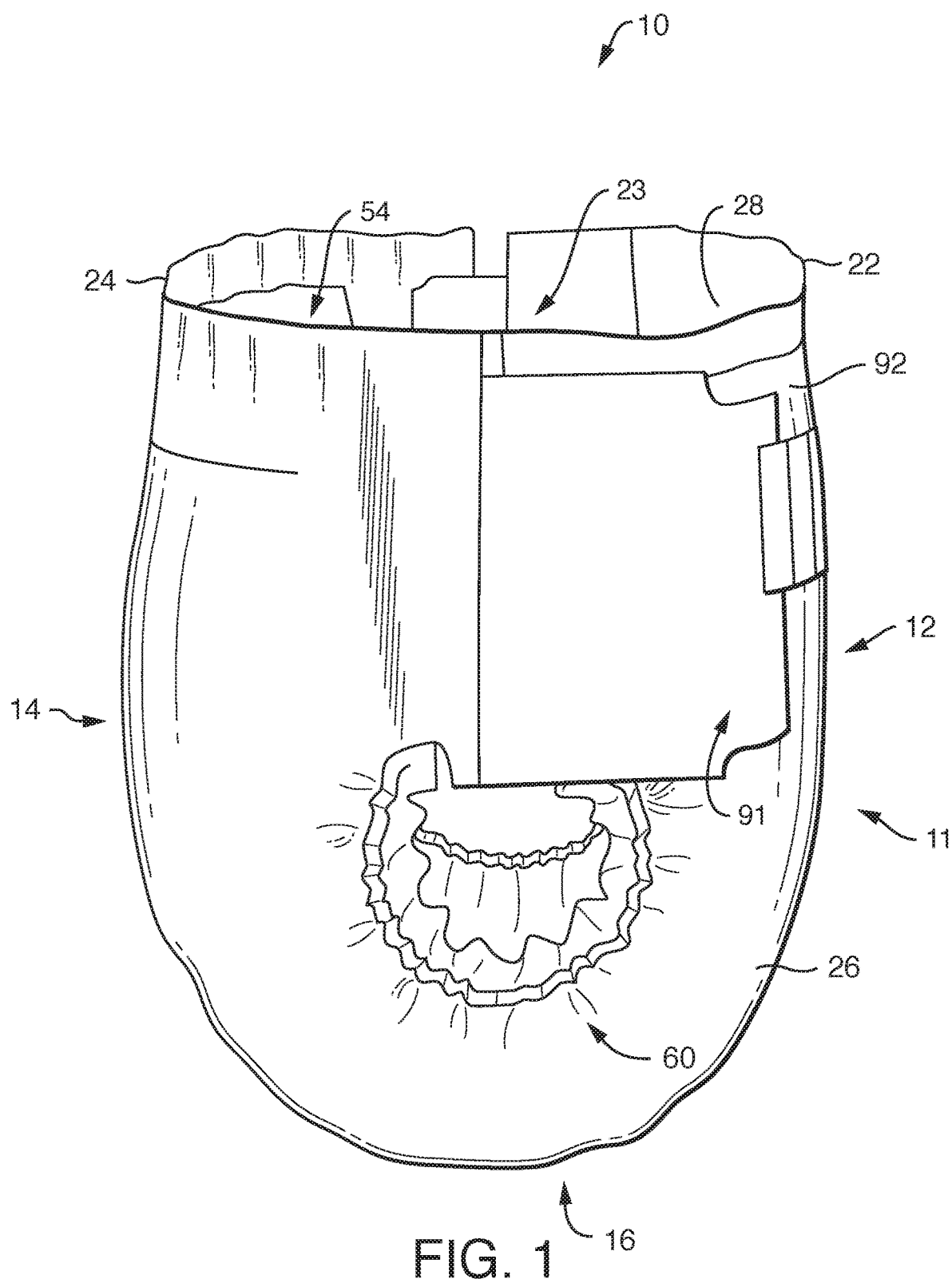
FIG. 1 is side perspective view of an exemplary embodiment of an absorbent article, such as a diaper, in a fastened condition.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards an absorbent article having a waist containment member. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded", "attached" or "coupled" refers herein to the joining, adhering, connecting, attaching, or the like, of two elements. Two elements will be considered bonded, attached or coupled together when they are joined, adhered, connected, attached, or the like, directly to one another or indirectly to one another, such as when each is directly bonded to intermediate elements. The bonding, attaching or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer liquids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, hydroentangling processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Absorbent Article:

Referring to FIGS. 1-4, a non-limiting illustration of an absorbent article 10 for example, a diaper, is illustrated. Other embodiments of the absorbent article could include training pants, youth pants, adult incontinence garments, and feminine hygiene articles. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure. For example, the absorbent article 310 in FIGS. 10 and 11 provides an exemplary embodiment of an absorbent article 310 that can be manufactured in cross-direction manufacturing process.

Figure 2:
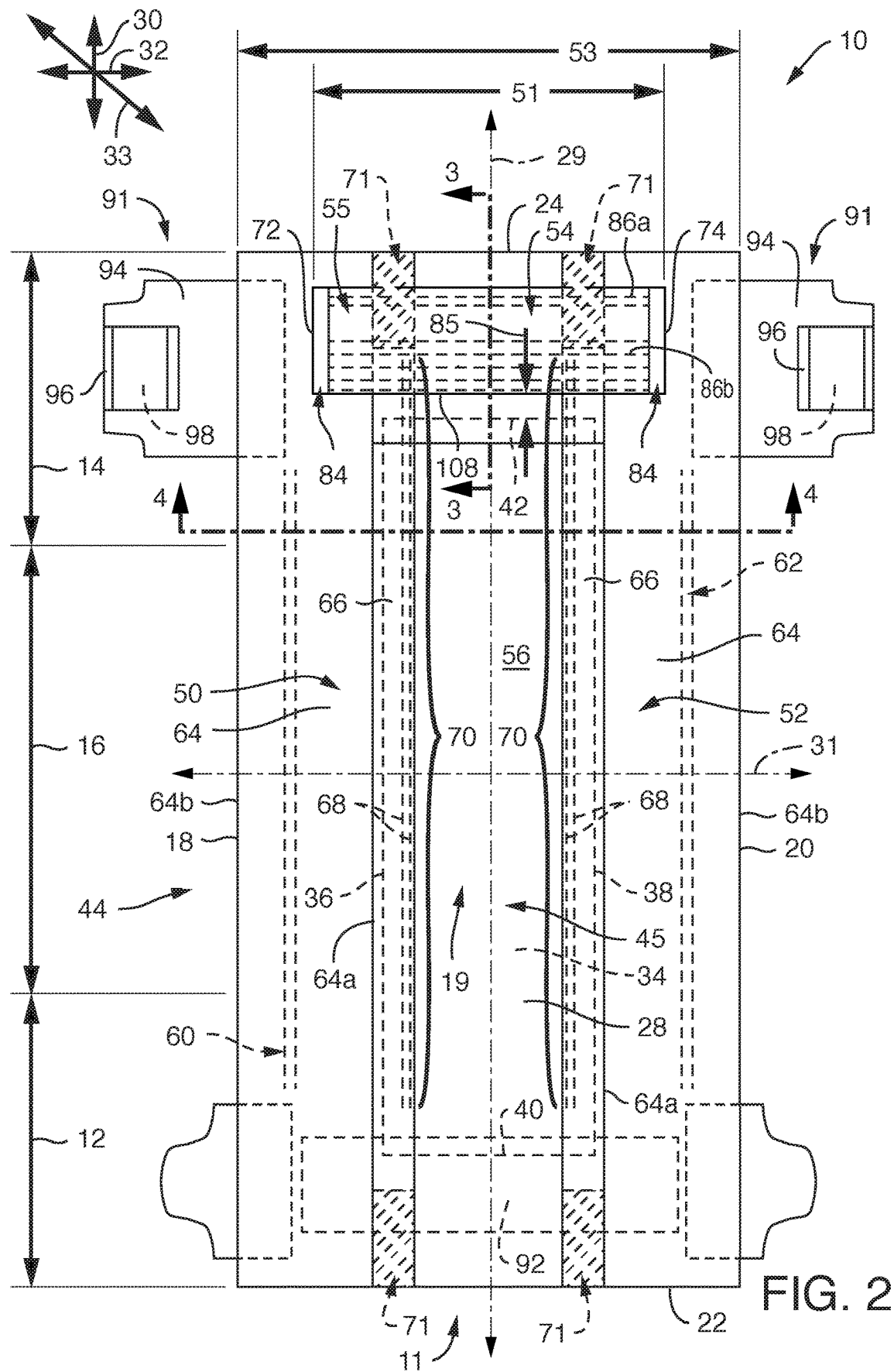
FIG. 2 is a top plan view of the absorbent article of FIG. 1 in a stretched, laid flat, unfastened condition.
Figure 10:
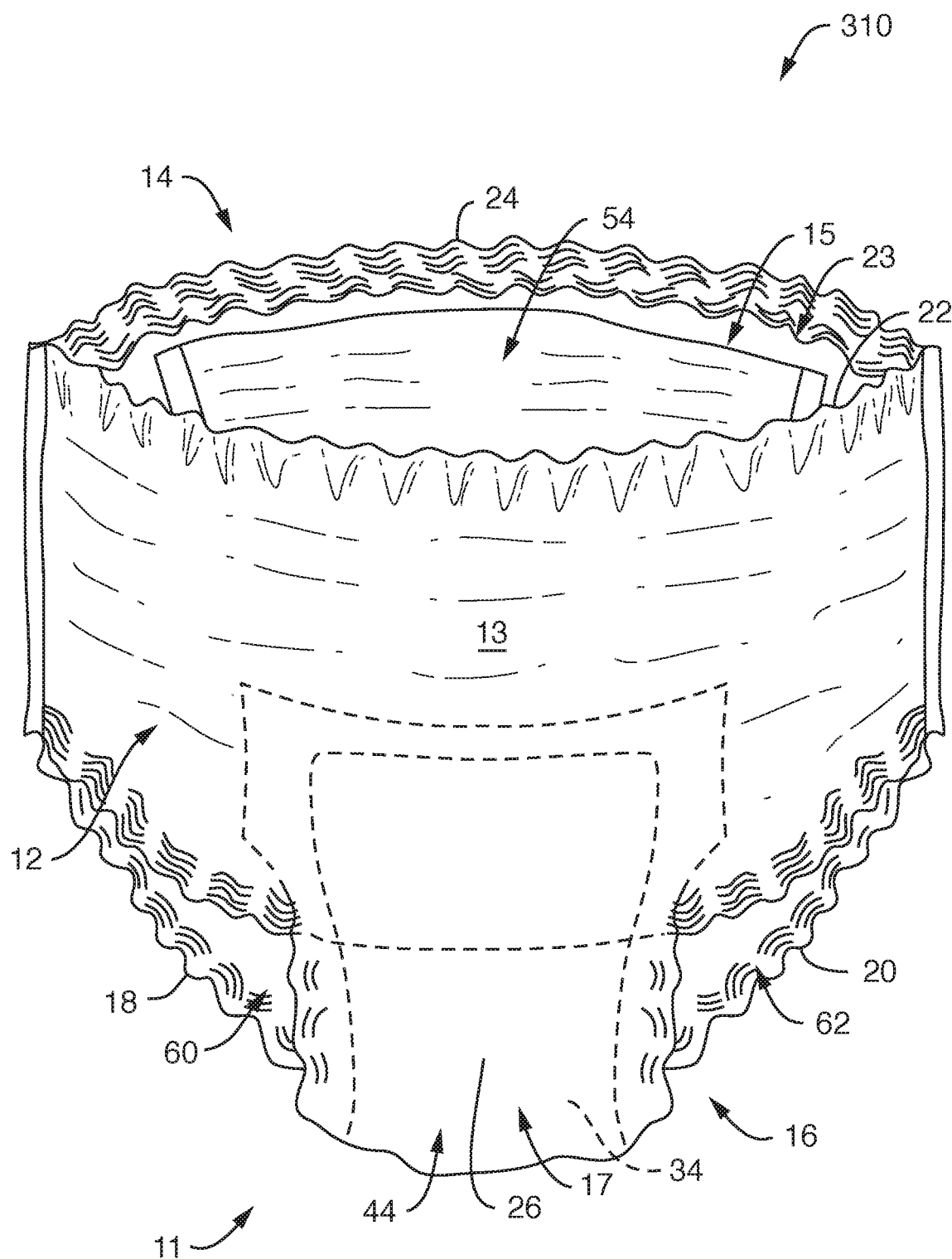
FIG. 10 is a front perspective view of an alternative embodiment of an absorbent article, such as a pant.
Figure 11:
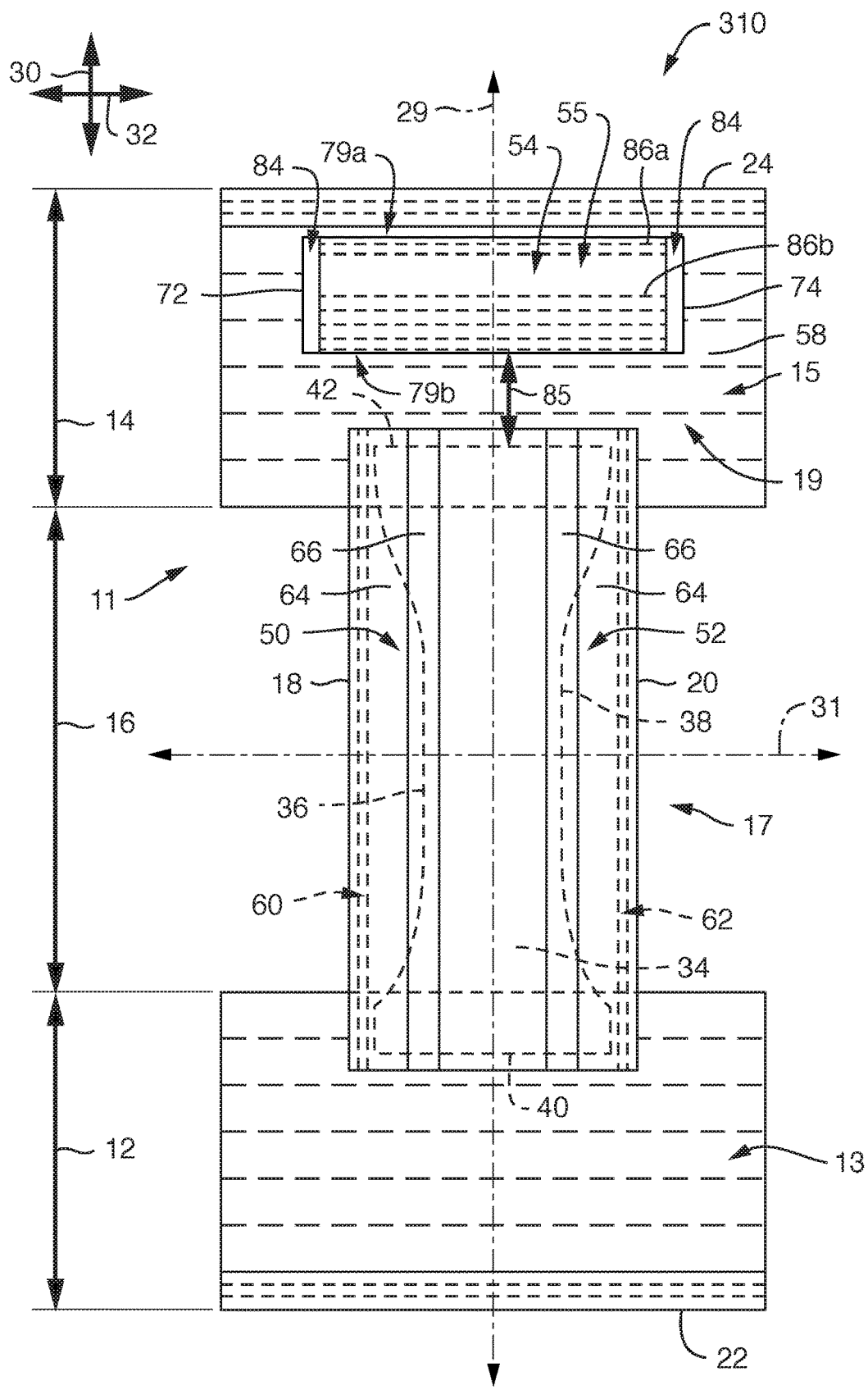
FIG. 11 is a top plan view of the absorbent article of FIG. 10 in a stretched, laid flat condition.

The absorbent article 10 illustrated in FIGS. 1 and 2, and the absorbent article 310 illustrated in FIGS. 10 and 11 can each include a chassis 11. The absorbent article 10, 310 can include a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region. In the embodiment depicted in FIGS. 10 and 11, a three-piece construction of an absorbent article 310 is depicted where the absorbent article 310 can have a chassis 11 including a front waist panel 13 defining the front waist region 12, a rear waist panel 15 defining the rear waist region 14, and an absorbent panel 17 defining the crotch region 16 of the absorbent article 310. The absorbent panel 17 can extend between the front waist panel 13 and the rear waist panel 15. In some embodiments, the absorbent panel 17 can overlap the front waist panel 13 and the rear waist panel 15. The absorbent panel 17 can be bonded to the front waist panel 13 and the rear waist panel 15 to define a three-piece construction. However, it is contemplated that an absorbent article can be manufactured in a cross-direction without being a three-piece construction garment which is also sometimes referred to as a one-piece construction (not shown) as the front waist panel 13 and the rear waist panel 15 are integral with one another by way of commonly connected components forming the waist panel such as a bodyside liner and/or an outercover which can envelope the absorbent panel 17 or simply cover the garment side of the absorbent panel 17.

The absorbent article 10, 310 can have a pair of longitudinal side edges 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24. The longitudinal side edges 18, 20 can extend in a direction parallel to the longitudinal direction 30 for their entire length, such as for the absorbent articles 10 illustrated in FIG. 2. In other embodiments, the longitudinal side edges 18, 20 can be curved between the front waist edge 22 and the rear waist edge 24. In the absorbent article 310 of FIGS. 10 and 11, the longitudinal side edges 18, 20 can include portions of the front waist panel 13, the absorbent panel 17, and the rear waist panel 15.

The front waist region 12 can include the portion of the absorbent article 10, 310 that, when worn, is positioned at least in part on the front of the wearer while the rear waist region 14 can include the portion of the absorbent article 10, 310 that, when worn, is positioned at least in part on the back of the wearer. The crotch region 16 of the absorbent article 10, 310 can include the portion of the absorbent article 10, 310 that, when worn, is positioned between the legs of the wearer and can partially cover the lower torso of the wearer. The waist edges, 22 and 24, of the absorbent article 10, 310 are configured to encircle the waist of the wearer and together define a central waist opening 23 (as labeled in FIG. 1 and FIG. 10) for the waist of the wearer. Portions of the longitudinal side edges 18, 20 in the crotch region 16 can generally define leg openings for the legs of the wearer when the absorbent article 10, 310 is worn.

Figure 3:
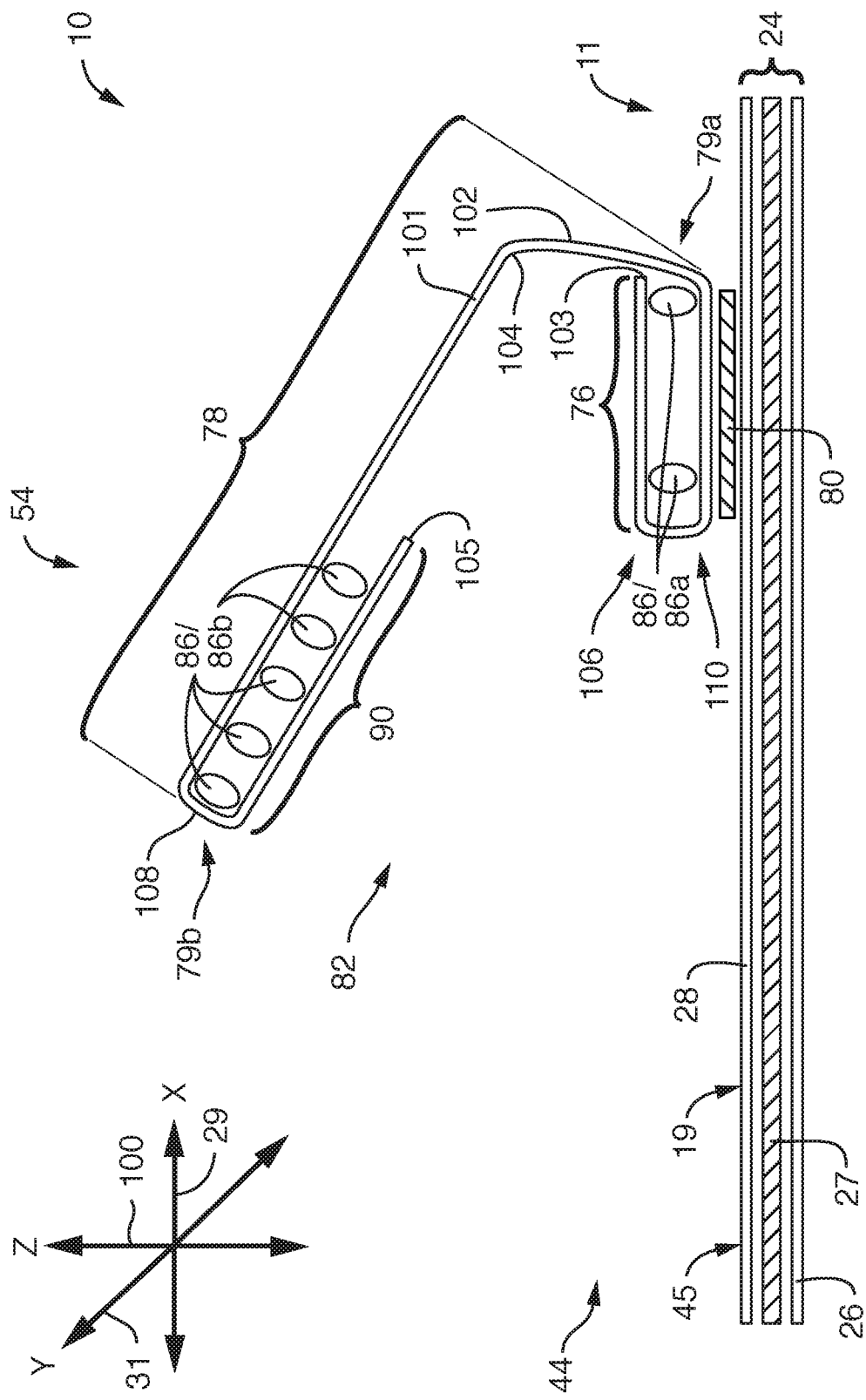
FIG. 3 is a cross-sectional view taken along line 3-3 from FIG. 2, but with the waist containment member being shown in a relaxed configuration.
Figure 4:
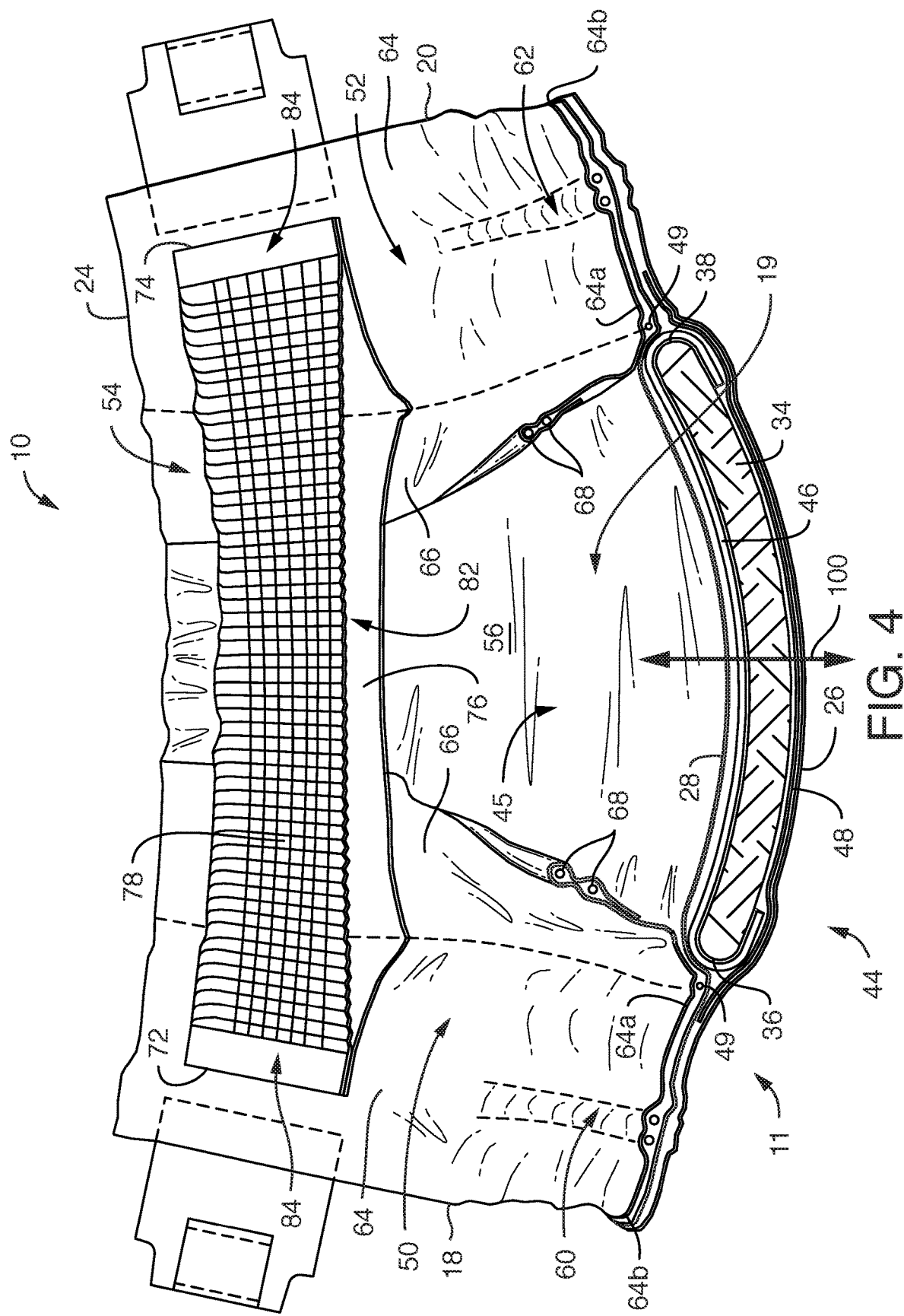
FIG. 4 is a front perspective cross-sectional view taken along line 4-4 from FIG. 2, with the absorbent article being in a relaxed configuration.

The absorbent article 10, 310 can include an outer cover 26 and a bodyside liner 28. The outer cover 26 and the bodyside liner 28 can form a portion of the chassis 11. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. As an example, FIG. 3 depicts the bodyside liner 28 bonded to the outer cover 26 with adhesive 27. The outer cover 26 can define a length in a longitudinal direction 30, and a width in the lateral direction 32, which, in the illustrated embodiment, can coincide with the length and width of the absorbent article 10. As illustrated in FIGS. 2 and 11, the absorbent article 10, 310 can have a longitudinal axis 29 extending in the longitudinal direction 30, and a lateral axis 31 extending in the lateral direction 32. The lateral axis 31 is located midway between the front waist edge 22 and the rear waist edge 24. As shown in FIGS. 3 and 4, the absorbent article 10 also has a vertical or z-direction axis 100 ending in the vertical direction 33.

The chassis 11 can include an absorbent body 34. The absorbent body 34 can be disposed between the outer cover 26 and the bodyside liner 28. The absorbent body 34 can have longitudinal edges, 36 and 38, which, in an embodiment, can form portions of the longitudinal side edges, 18 and 20, respectively, of the absorbent article 10, 310. The absorbent body 34 can have a first end edge 40 that is opposite a second end edge 42, respectively, which, in an embodiment, can form portions of the waist edges, 22 and 24, respectively, of the absorbent article 10. In some embodiments, the first end edge 40 can be in the front waist region 12. In some embodiments, the second end edge 42 can be in the rear waist region 14. In an embodiment, the absorbent body 34 can have a length and width that are the same as or less than the length and width of the absorbent article 10, 310. The bodyside liner 28, the outer cover 26, and the absorbent body 34 can form part of an absorbent assembly 44. In the absorbent article 310 of FIGS. 10 and 11, the absorbent panel 17 can form the absorbent assembly 44. The absorbent assembly 44 can also include a fluid transfer layer 46 (as shown in FIG. 4) and a fluid acquisition layer (not shown) between the bodyside liner 28 and the fluid transfer layer 46 as is known in the art. The absorbent assembly 44 can also include a spacer layer 48 (as shown in FIG. 4) disposed between the absorbent body 34 and the outer cover 26.

The absorbent article 10, 310 can be configured to contain and/or absorb liquid, solid, and semi-solid body exudates discharged from the wearer. In some embodiments, containment flaps 50, 52 can be configured to provide a barrier to the lateral flow of body exudates. To further enhance containment and/or absorption of body exudates, the absorbent article 10, 310 can suitably include a waist containment member 54. In some embodiments, the waist containment member 54 can be disposed in the rear waist region 14 of the absorbent article 10, 310. Although not depicted herein, it is contemplated that the waist containment member 54 can be additionally or alternatively disposed in the front waist region 12 of the absorbent article 10, 310.

The waist containment member 54 can be disposed on the body facing surface 19 of the chassis 11 to help contain and/or absorb body exudates. In some embodiments, such as in the absorbent article 10 depicted in FIGS. 2 and 4, the waist containment member 54 can be disposed on the body facing surface 45 of the absorbent assembly 44. In some embodiments, the waist containment member 54 can be disposed on the body facing surface 56 of the bodyside liner 28. In some embodiments, such as in the absorbent article 310 depicted in FIGS. 10 and 11, the waist containment member 54 can be disposed on the body facing surface 58 of the rear waist panel 15.

The absorbent article 10, 310 can further include leg elastic members 60, 62 as are known to those skilled in the art. The leg elastic members 60, 62 can be attached to the outer cover 26 and/or the bodyside liner 28 along the opposite longitudinal side edges, 18 and 20, and positioned in the crotch region 16 of the absorbent article 10, 310. The leg elastic members 60, 62 can be parallel to the longitudinal axis 29 as shown in FIGS. 2 and 11 or can be curved as is known in the art. The leg elastic members 60, 62 can provide elasticized leg cuffs.

Additional details regarding each of these elements of the absorbent article 10, 310 described herein can be found below and with reference to the FIGS. 1-11.

Outer Cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent article 10, 310. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In some embodiments, the outer cover 26 can be a two layer construction, including an outer layer (not shown) and an inner layer (not shown) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer of the outer cover 26 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer of an outer cover 26 can be a 20 gsm spunbond polypropylene non-woven web. The outer layer may also be constructed of the same materials from which the bodyside liner 28 can be constructed as described herein.

The liquid impermeable inner layer of the outer cover 26 (or the liquid impermeable outer cover 26 where the outer cover 26 is of a single-layer construction) can be either vapor permeable (i.e., "breathable") or vapor impermeable. The liquid impermeable inner layer (or the liquid impermeable outer cover 26 where the outer cover 26 is of a single-layer construction) can be manufactured from a thin plastic film. The liquid impermeable inner layer (or the liquid impermeable outer cover 26 where the outer cover 26 is of a single-layer construction) can inhibit liquid body exudates from leaking out of the absorbent article 10, 310 and wetting articles, such as bed sheets and clothing, as well as the wearer and caregiver.

In some embodiments, where the outer cover 26 is of a single layer construction, it can be embossed and/or matte finished to provide a more cloth-like texture or appearance. The outer cover 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer (infants to adults) and the liquid loading imparted by the intended use of the absorbent article 10, 310. The absorbent body 34 can have a length and width that can be less than or equal to the length and width of the absorbent article 10, 310.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In an embodiment, the absorbent body 34 may be constructed of a single layer of materials, or in the alternative, may be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 34 can be free of superabsorbent material or in an alternate embodiment be comprised entirely of superabsorbent material.

If a spacer layer 48 is present, the absorbent body 34 can be disposed on the spacer layer 48 and superposed over the outer cover 26. The spacer layer 48 can be bonded to the outer cover 26, for example, by adhesive. In some embodiments, a spacer layer 48 may not be present and the absorbent body 34 can directly contact the outer cover 26 and can be directly bonded to the outer cover 26. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In some embodiments, at least a portion of a layer, such as but not limited to, a fluid transfer layer 46 and/or a spacer layer 48, can be positioned between the absorbent body 34 and the outer cover 26, such as illustrated in FIG. 4. The absorbent body 34 can be bonded to the fluid transfer layer 46 and/or the spacer layer 48. Typically the absorbent body 34 will be completely enveloped by a core wrap material such as a tissue wrap or a nonwoven material such a meltblown web, a spunbond web or both.

Bodyside Liner:

The bodyside liner 28 of the absorbent article 10, 310 can overlay the absorbent body 34 and the outer cover 26 and can isolate the wearer's skin from liquid waste retained by the absorbent body 34. In various embodiments, a fluid transfer layer 46 can be positioned between the bodyside liner 28 and the absorbent body 34. In various embodiments, an acquisition layer (not shown) can be positioned between the bodyside liner 28 and the absorbent body 34 or a fluid transfer layer 46, if present. In various embodiments, the bodyside liner 28 can be bonded to the acquisition layer, or to the fluid transfer layer 46 if no acquisition layer is present, via adhesive and/or by a point fusion bonding. The point fusion bonding may be selected from ultrasonic, thermal, pressure bonding, and combinations thereof.

In an embodiment, the bodyside liner 28 can extend beyond the absorbent body 34 and/or a fluid transfer layer 46, if present, and/or an acquisition layer, if present, and/or a spacer layer 48, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. It is contemplated that the bodyside liner 28 may be narrower than the outer cover 26. However, in other embodiments, the bodyside liner 28 and the outer cover 26 may be of the same dimensions in width and length, for example, as depicted in the embodiments illustrated in FIG. 1. In other embodiments, the bodyside liner 28 can be of greater width than the outer cover 26. It is also contemplated that the bodyside liner 28 may not extend beyond the absorbent body 34 and/or may not be secured to the outer cover 26. In some embodiments, the bodyside liner 28 can wrap at least a portion of the absorbent body 34, including wrapping around both longitudinal edges 36, 38 of the absorbent body 34, and/or one or more of the end edges 40, 42. It is further contemplated that the bodyside liner 28 may be composed of more than one segment of material. The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentagled. The projection layer can include hollow projections, such as those disclosed in U.S. Patent Application Publication No. 2014/0121623 to Kirby et al.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from about 10 or 12 to about 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent article 10, 310. In other aspects, the bodyside liner 28 can be stretchable, and more suitably elastic, in both the lateral and the longitudinal directions 32, 30, respectively.

Containment Flaps:

In an embodiment, the absorbent article 10, 310 can include a pair of containment flaps 50, 52. The containment flaps 50, 52 can be formed separately from the absorbent chassis 11 and attached to the chassis 11 or can be formed integral to the chassis 11. In some embodiments, the containment flaps 50, 52 can be secured to the chassis 11 of the absorbent article 10, 310 in a generally parallel, spaced relation with each other laterally inward of the leg openings to provide a barrier against the flow of body exudates. One containment flap 50 can be on a first side of the longitudinal axis 29 and the other containment flap 52 can be on a second side of the longitudinal axis 29. In an embodiment, the containment flaps 50, 52 can extend generally in a longitudinal direction 30 from the front waist region 12 of the absorbent article 10, through the crotch region 16 to the rear waist region 14 of the absorbent article 10. In some embodiments, the containment flaps 50, 52 can extend in a direction substantially parallel to the longitudinal axis 29 of the absorbent article 10, however, in other embodiments, the containment flaps 50, 52 can be curved, as is known in the art. In other embodiments, such as the absorbent article 310 in FIGS. 10 and 11, the containment flaps 50, 52 can be disposed on the absorbent panel 17 in the crotch region 16.

In embodiments where the containment flaps 50, 52 are coupled to the chassis 11, the containment flaps 50, 52 can be bonded to the bodyside liner 28 with a barrier adhesive 49, as shown in FIG. 4. 4 or the containment flaps 50, 52 can be bonded to the outer cover 26 with a barrier adhesive 49 in some embodiments where the bodyside liner 28 does not extend the full lateral width of the outer cover 26. Of course, the containment flaps 50, 52 can be bonded to other components of the chassis 11 and can be bonded with other suitable means other than a barrier adhesive 49. The containment flaps 50, 52 can be constructed of a fibrous material which can be similar to the material forming the bodyside liner 28. Other conventional materials, such as polymer films, can also be employed.

The containment flaps 50, 52 can each include a base portion 64 and a projection portion 66. The base portion 64 can be bonded to the chassis 11, for example, to the bodyside liner 28 or the outer cover 26 as mentioned above. The base portion 64 can include a proximal end 64a and a distal end 64b. The projection portion 66 can be separated from the base portion 64 at the proximal end 64a of the base portion 64. As used in this context, the projection portion 66 is separated from the base portion 64 at the proximal end 64a of the base portion 64 in that the proximal end 64a of the base portion 64 defines a transition between the projection portion 66 and the base portion 64. The proximal end 64a of the base portion 64 can be located near the barrier adhesive 49. In some embodiments, the distal ends 64b of the base portion 64 can laterally extend to the respective longitudinal side edges 18, 20 of the absorbent article 10. In other embodiments, the distal ends 64b of the base portion 64 can end laterally inward of the respective longitudinal side edges 18, 20 of the absorbent article 10, 310. The containment flaps 50, 52 can also each include a projection portion 66 that is configured to extend away from the body facing surface 19 of the chassis 11 at least in the crotch region 16 when the absorbent article 10 is in a relaxed configuration, as illustrated in FIG. 4.

The containment flaps 50, 52 can include a tack-down region 71 in either or both of the front waist region 12 and the rear waist region 14 where the projection portion 66 is coupled to the body facing surface 19 of the chassis 11.

It is contemplated that the containment flaps 50, 52 can be of various configurations and shapes, and can be constructed by various methods. For example, the containment flaps 50, 52 of FIG. 2 depict a vertical containment flap 50, 52 with a tack-down region 71 in both the front and rear waist regions 12, 14 where the projection portion 66 of each containment flap 50, 52 is tacked down to the bodyside liner 28 towards or away from the longitudinal axis 29 of the absorbent article 10. However, the containment flaps 50, 52 can include a tack-down region 71 where the projection portion 66 of each of the containment flaps 50, 52 is folded back upon itself and coupled to itself and the bodyside liner 28 in a "C-shape" configuration, as is known in the art and described in U.S. Pat. No. 5,895,382 to Robert L. Popp et al. As yet another alternative, it is contemplated that the containment flaps 50, 52 could be constructed in a "T-shape" configuration, such as described in U.S. patent application Ser. No. 13/900,134 by Robert L. Popp et al., which published as U.S. Patent Application Publication 2014/0350504. Such a configuration can also include a tack-down region 71 in either or both of the front and rear waist regions 12, 14, respectively. Of course, other configurations of containment flaps 50, 52 can be used in the absorbent article 10, 310 and still remain within the scope of this disclosure.

The containment flaps 50, 52 can include one or more flap elastic members 68, such as the two flap elastic strands depicted in FIGS. 2 and 4. Suitable elastic materials for the flap elastic members 68 can include sheets, strands or ribbons of natural rubber, synthetic rubber, or thermoplastic elastomeric materials. Of course, while two elastic members 68 are shown in each containment flap 50, 52, it is contemplated that the containment flaps 50, 52 can be configured with one or three or more elastic members 68. Alternatively or additionally, the containment flaps 50, 52 can be composed of a material exhibiting elastic properties itself.

The flap elastic members 68, as illustrated in FIGS. 2 and 4, can have two strands of elastomeric material extending longitudinally in the projection portion 66 of the containment flaps 50, 52, in generally parallel, spaced relation with each other. The elastic members 68 can be within the containment flaps 50, 52 while in an elastically contractible condition such that contraction of the strands gathers and shortens the projection portions 66 of the containment flaps 50, 52 in the longitudinal direction 30. As a result, the elastic members 68 can bias the projection portions 66 of the containment flaps 50, 52 to extend away from the body facing surface 45 of the absorbent assembly 44 in a generally upright orientation of the containment flaps 50, 52, especially in the crotch region 16 of the absorbent article 10, when the absorbent article 10 is in a relaxed configuration.

During manufacture of the containment flaps 50, 52 at least a portion of the elastic members 68 can be bonded to the containment flaps 50, 52 while the elastic members 68 are elongated. The percent elongation of the elastic members 68 can be, for example, about 110% to about 350%. The elastic members 68 can be coated with adhesive while elongated to a specified length prior to attaching to the elastic members 68 to the containment flaps 50, 52. In a stretched condition, the length of the elastic members 68 which have adhesive coupled thereto can provide an active flap elastic region 70 in the containment flaps 50, 52, as labeled in FIG. 2, which will gather upon relaxation of the absorbent article 10. The active flap elastic region 70 of containment flaps 50, 52 can be of a longitudinal length that is less than the length of the absorbent article 10, 310. In this exemplary method of bonding the elastic members 68 to the containment flaps 50, 52, the portion of the elastic members 68 not coated with adhesive will retract after the elastic members 68 and the absorbent article 10 are cut in manufacturing to form an individual absorbent article 10. As noted above, the relaxing of the elastic members 68 in the active flap elastic region 70 when the absorbent article 10, 310 is in a relaxed condition can cause each containment flap 50, 52 to gather and cause the projection portion 66 of each containment flap 50, 52 to extend away from the body facing surface 19 of the chassis 11 (e.g., the body facing surface 45 of the absorbent assembly 44 or the body facing surface 56 of the bodyside liner 28), as depicted in FIG. 4.

Of course, the elastic members 68 can be bonded to the containment flaps 50, 52 in various other ways as known by those of skill in the art to provide an active flap elastic region 70, which is within the scope of this disclosure. Additionally, the active flap elastic regions 70 can be shorter or longer than depicted herein, including extending to the front waist edge 22 and the rear waist edge 24, and still be within the scope of this disclosure.

Leg Elastics:

Leg elastic members 60, 62 can be secured to the outer cover 26, such as by being bonded thereto by laminate adhesive, generally laterally inward of the longitudinal side edges, 18 and 20, of the absorbent article 10, 310. The leg elastic members 60, 62 can form elasticized leg cuffs that further help to contain body exudates. In an embodiment, the leg elastic members 60, 62 may be disposed between inner and outer layers (not shown) of the outer cover 26 or between other layers of the absorbent article 10, for example, between the base portion 64 of each containment flap 50, 52 and the bodyside liner 28 as depicted in FIG. 4, between the base portion 64 of each containment flap 50, 52 and the outer cover 26, or between the bodyside liner 28 and the outer cover 26. The leg elastic members 60, 62 can be one or more elastic components near each longitudinal side edge 18, 20. For example, the leg elastic members 60, 62 as illustrated herein each include two elastic strands. A wide variety of elastic materials may be used for the leg elastic members 60, 62. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 60, 62 can be formed with the containment flaps 50, 52, and then attached to the chassis 11 in some embodiments. Of course, the leg elastic members 60, 62 can be omitted from the absorbent article 10, 310 without departing from the scope of this disclosure.

Waist Containment Member:

In an embodiment, the absorbent article 10, 310 can have one or more waist containment members 54. FIGS. 1-4, 10, and 11 depict an absorbent article 10, 310 with an embodiment of a waist containment member 54.

The waist containment member 54 can be disposed in the rear waist region 14 as illustrated in FIGS. 1-4, 10 and 11. As will be discussed in more detail below, the waist containment member 54 can help contain and/or absorb body exudates, especially low viscosity fecal matter, and as such, can be preferred to be in the rear waist region 14. In some embodiments, the absorbent article 10, 310 can have a waist containment member 54 disposed in the front waist region 12. A waist containment member 54 in the front waist region 12 can help contain and/or absorb body exudates, such as urine, in the front waist region 12. Although not as prevalent as in the rear waist region 14, in some circumstances, fecal material may also spread to the front waist region 12, and thus, a waist containment member 54 disposed in the front waist region 12 can help contain and/or absorb body exudates as well. In other embodiments, the absorbent article 10, 310 can have a waist containment member 54 in both the rear waist region 14 and the front waist region 12.

In some embodiments, the waist containment member 54 can be disposed on the body facing surface 45 of the absorbent assembly 44. In some embodiments, such as in embodiments illustrated in FIGS. 1-4, the waist containment member 54 can be disposed on the body facing surface 56 of the bodyside liner 28. However, in some embodiments, such as the absorbent article 310 in FIG. 11, the waist containment member 54 can be disposed on a body facing surface 58 of the rear waist panel 15 of the chassis 11.

The waist containment member 54 is made from a waist containment material 101 and can include a first longitudinal side edge 72, a second longitudinal side edge 74, a waist containment first end edge 103 and a waist containment second edge 105 joining the first longitudinal edge 72 and the second longitudinal edge 74. The waist containment member 54 has a first surface 102 which is designed to come in contact with the body of the wearer and a second surface 104 opposite the first surface 102. The first longitudinal side edge 72 can be opposite from the second longitudinal side edge 74. The distance between the first longitudinal side edge 72 and the second longitudinal side edge 74 can define a width 51 of the waist containment member 54 in the lateral direction 32, as shown in FIG. 2. Although not depicted, in some embodiments, the first longitudinal side edge 72 can substantially align with the first longitudinal side edge 18 of the absorbent article 10. Similarly, in some embodiments, the second longitudinal side edge 74 can align with the second longitudinal side edge 20 of the absorbent article 10. As illustrated in FIGS. 2 and 11, the waist containment member 54 can be configured such that the first longitudinal side edge 72 can be disposed laterally outward of the proximal end 64a of the base portion 64 of the containment flap 50. Similarly, the waist containment member 54 can be configured such that the second longitudinal side edge 74 can be disposed laterally outward of the proximal end 64a of the base portion 64 of the containment flap 52.

In various embodiments, the waist containment member 54 can also include a proximal portion 76 and a distal portion 78. The proximal portion 76 can be coupled to the body facing surface 19 of chassis 11 (e.g., the body facing surface 45 of the absorbent assembly 44 or the body facing surface 56 of the bodyside liner 28) whereas the distal portion 78 or at least a portion of the distal portion of the waist containment member 54 can be free to move with respect to the chassis 11 and the absorbent assembly 44 when the absorbent article 10, 310 is in the relaxed configuration, such as shown in FIG. 4. FIG. 3 provides a cross-sectional view of the waist containment member 54 of FIG. 2 in a relaxed configuration, such that the distal portion 78 can be seen extending away from the chassis 11 and absorbent assembly 44 in a vertical direction 33 along the vertical axis 100, which is perpendicular to the plane defined by the longitudinal axis 29 and the lateral axis 31. A first fold 79a can separate the proximal portion 76 from the distal portion 78 in the various embodiments of the waist containment member 54 discussed herein. As used in this context, the first fold 79a separates the proximal portion 76 from the distal portion 78 in that the first fold 79a defines a transition between the proximal portion 76 and the distal portion 78 in the containment member material 101 and the containment member 54 as a whole. In alternate embodiments (not shown) the proximal portion 76 and the distal portion 78 can be made from separate materials which are attached to one another such as, for example, in the area of the first fold 79a or in lieu of the first fold 79a. The physical form of the attachment may be, for example, by way of a butt seam or a lap seam. The first fold line 79a, as with the other fold lines discussed below, extends is the direction of the lateral axis 31 meaning that the fold line runs in a direction generally parallel to the lateral axis 31 and thus generally perpendicular to the longitudinal axis 29.

The proximal portion 76 can be coupled to the body facing surface 19 of the chassis 11 with an adhesive 80, and in some embodiments, the proximal portion 76 can be coupled to the body facing surface 45 of the absorbent assembly 44. In some embodiments, such as in embodiments illustrated in FIGS. 2-4, the proximal portion 76 of the waist containment member 54 can be coupled to the body facing surface 56 of the bodyside liner 28. However, in some embodiments, such as the absorbent article 310 in FIG. 11, the proximal portion 76 of the waist containment member 54 can be coupled to the body facing surface 58 of the rear waist panel 15. As illustrated in the examples shown in FIG. 3, the proximal portion 76 can be coupled to the body facing surface 45 of the absorbent assembly 44 with adhesive 80 along the entire length of the proximal portion 76 in the longitudinal direction 30, however, it can be contemplated that only a portion of the proximal portion 76 in the longitudinal direction 30 is coupled to the body facing surface 45 of the absorbent assembly 44. Of course, it is contemplated that the proximal portion 76 of the waist containment member 54 can be coupled to the body facing surface 19 of the chassis 11 or the body facing surface 45 of the absorbent assembly 44 by means other than an adhesive 80, such as by pressure bonding, ultrasonic bonding, thermal bonding, and combinations thereof. In preferred embodiments, the proximal portion 76 is coupled to the body facing surface 19 of the chassis 11 in the lateral direction 32 in a constant fashion along the lateral axis 31, as opposed to an intermittent fashion, such that a barrier to body exudates is formed between the proximal portion 76 and the body facing surface 19 of the chassis 11.

The proximal portion 76 of the waist containment member 54 can include a longitudinal length measured in the longitudinal direction 30 along the longitudinal axis 29 that is shorter than a longitudinal length of the distal portion 78 of the waist containment member 54 (not shown). However in some embodiments, the longitudinal length of the proximal portion 76 can be substantially equal to or larger than the longitudinal length of the distal portion 78 of the waist containment member 54. For purposes herein, the longitudinal length of the proximal portion 76 and the longitudinal length of the distal portion 78 of the waist containment member 54 are measured when the absorbent article 10, 310 is in the stretched, laid flat configuration. It can be appreciated that the relative longitudinal lengths of the proximal portion 76 and the distal portion 78 can be varied between embodiments of the waist containment member 54 without departing from the scope of this disclosure.

The width 51 of the proximal portion 76 and the distal portion 78 can be the same or different from one another. The proximal portion 76 has a proximal portion lateral width as measured between the first longitudinal side edge 72 and the second longitudinal side edge 74. In a similar fashion, the distal portion 78 has a distal portion lateral width as measured between the first longitudinal side edge 72 and the second longitudinal side edge 74. In an embodiment, the proximal portion lateral width can be equal to the distal portion lateral width. In an embodiment, the proximal portion lateral width can be greater than the distal portion lateral width. For example, the proximal portion lateral width can be between about 10 percent and about 40 percent greater than the distal portion lateral width. Alternatively, the proximal portion lateral width can be between about 20 percent and about 30 percent greater than the distal portion lateral width. The determination of such width differences is determined when the absorbent article 10 is in a stretched, laid-flat configuration. Thus, for example, if the proximal portion 76 had a proximal portion lateral width of 110 mm and the distal portion 78 had a distal portion lateral width of 100 mm, the proximal portion width would be 10 percent greater than the distal portion. The variation in width can be accomplished in a number of ways. In an embodiment, the longitudinal side edges 72 and 74 can be cut in a non-linear fashion or the longitudinal side edges 72 and 74 can be folded to reduce the width of one portion as opposed to another. In another embodiment, the proximal portion 76 can be formed from a different material having a different lateral dimension than that of the distal portion 78. When two or more different materials are used, they can be attached to one another by any suitable means such as, but not limited to, adhesives, ultrasonic bonds, thermal bonds, pressure bonds, or other conventional techniques. Such attachment can take place in the area of the first fold 79a or at other locations in the waist containment member 54.

As illustrated in FIG. 3, because the distal portion 78 of the waist containment member 54 can freely move with respect to the absorbent assembly 44 when the absorbent article 10, is in the relaxed configuration, the distal portion 78 can help provide a containment pocket 82 when the absorbent article 10 is in the relaxed configuration when being worn by the wearer. The containment pocket 82 can help provide a barrier to contain and/or can help absorb body exudates. The containment pocket 82 can be especially beneficial for containing and/or absorbing low viscosity fecal matter, which can be prevalent in younger children.

The first longitudinal side edge 72 can be disposed laterally outward of the proximal end 64a of the base portion 64 of the containment flap 50, and thus, the pocket 82 can extend laterally outward of the proximal end 64a of the containment flap 50. Similarly, the second longitudinal side edge 74 can be disposed laterally outward of the proximal end 64a of the base portion 64 of the containment flap 52 and the pocket 82 can extend laterally outward of the proximal end 64a of the containment flap 52. Such a configuration provides waist containment member 54 with a wide containment pocket 82 to contain and/or absorb body exudates. To help prevent lateral flow of body exudates that are contained by the containment pocket 82 of the waist containment member 54, the distal portion 78 of the waist containment member 54 can be bonded to the proximal portion 76 of the waist containment member 54 and/or the body facing surface 19 of the chassis 11 near the first and second longitudinal side edges 72, 74, respectively. For example, FIGS. 2, 4 and 11 depict tack-down regions 84 where the distal portion 78 of the waist containment member 54 can be bonded to the proximal portion 76 of the waist containment member 54 and/or the body facing surface 19 of the chassis 11 near the first and second longitudinal side edges 72, 74, respectively.

In some embodiments, the width 51 of the waist containment member 54 in the lateral direction 32 as compared to the width 53 of the chassis 11 (as labeled in FIG. 2) can have a ratio of about 0.85 to about 1.00. In some embodiments, the width 51 of the waist containment member 54 in the lateral direction 32 as compared to the width 53 of the chassis 11 can have a ratio of about 0.87 to about 1.00. And in other embodiments, the width 51 of the waist containment member 54 in the lateral direction 32 as compared to the width 53 of the chassis 11 can have a ratio of about 0.90 to about 1.00. For purposes herein, the width 53 of the chassis 11 for use in this ratio is the width 53 of the chassis 11 in the waist region in which the waist containment member 54 is disposed and both width measurements are taken in a direction parallel to the lateral direction 32. Thus, for the examples illustrated herein, the width 51 of the waist containment member 54 can be compared to the width 53 of the chassis 11 in the rear waist region 14. Additionally, the width 51 of the waist containment member 54 in the lateral direction 32 and the width 53 of the chassis 11 as discussed for the ratios herein are to be measured when the absorbent article 10, 310 is in the stretched, laid flat configuration.

As previously discussed a problem with current absorbent articles employing pocketing systems to trap body exudates and in particular runny bowel movements is the fact that they do not provide as tight as fit as is ultimately desired especially between the rear waist region 14 and the rear waist edge 24 and the gluteal depression located in the rear torso of a wearer of absorbent articles such as are disclosed and discussed herein. Research has indicated that several aspects of absorbent article designs contribute to poor fit and leakage of such runny exudates. First is the location of the elastic materials used to create tension in the absorbent article and the second is the effect of the tension so applied to the materials of the absorbent article. Commonly, the most economical materials used to create tension in such absorbent articles are elastic strand materials such as Lycra® strands, round or flat pieces of natural rubber, elastic films and/or strips of elastic films. Typically, such elastic materials are encased in other softer layers of material such as layers of fibrous nonwoven webs—spunbond webs, meltblown webs and bonded carded staple fiber webs being but a few examples. The elastic materials are formed into laminates with outer layers of fibrous nonwoven web forming the exterior layers of the laminate and the elastic material forming the interior layer. In one, non-limiting example, the elastics can be stretched and then affixed to the external layers while in the stretched state with adhesives or other techniques. Once the elastics are affixed and the adhesive has dried, the laminate is allowed to relax thereby causing the laminate to retract and the external layers to form gathers. Alternatively, the elastics can be laid down in an un-tensioned configuration and attached to two external layers of material, such as, for example, bonded carded webs, thereby forming an elastic laminate. After lamination, the laminate can be subjected to a stretching process such a grooved rolling to partially break the bonds of the cared web and imparting elasticity to the overall laminate.

Depending on a series of factors including the amount of retraction, the basis weights of the nonwoven layers, the degree of bonding of the elastics to the external layers and other factors, the gathers so formed in the laminate can form peaks and valley which provide fluid pathways via the valleys for the body exudates to escape between the body facing surface of the absorbent article and the skin of the wearer. Because of the degree of body curvature in the area of the gluteal depression, the propensity for leakage can be increased.

The design of the present invention allows the creation of an absorbent article which still employs such waist-pocketing techniques but reduces the tendency for leakage and undesirable design traits. First, as will be discussed in further detail below, the waist containment member 54 according to the present invention employs elastic members 86 in its proximal portion 76 where the waist containment member 54 is attached to the chassis 11 in the area of the absorbent article 10, 310 more closely associated with the central waist opening 23. Optionally, elastic members 86 can be located in its distal portion 78.

If past product designs which formed pockets did not utilize elastics in the proximal portion 76 of the waist containment member 54 located adjacent the rear waist edge 24, the elastics 86 located only in the distal portion 78 tended to relocate the elastic tension in the rear waist region 14 from a form in which the elastic tension was applied continuously along the width 53 of the chassis 11 to only being attached at two points near the outside ears where the back fasteners 91 were located. Because the tension was only pulling on the ears, the ears tended to fold in when not being pulled. This could result in the absorbent article being slightly more difficult to apply by the consumer.

A second problem was that the previous designs posed an aesthetic fault when looking at the back of the product when positioned on the wearer. It was determined that such designs did not have elasticity high up on the back of the product, thereby allowing the back waist edge to pull away from the skin of the wearer and form a gap between the waist and the wearer. The present invention's utilization of elastic members 86 in the proximal portion 76, results in the waist tension being more uniformly distributed across the entire width of the waist area of the absorbent article 10 adjacent the rear waist edge 24 and/or adjacent the front waist edge 22 when a waist containment member 54 is located in the front waist region 12.

In addition, as can be seen from the cross-section of FIG. 3, the elastic members 86a located near the waist edge, in this case the rear waist edge 24, are located below the outermost layer of the waist containment member 54 which is non-elasticized. As a result, it has been found that this external layer of material directly overlaying the elastic members 86 is able to make a better seal with the skin of the wearer as it is less prone to having the number or degree of gathers that, as described above, are typically associated with normal elastic configurations located in the waist region of such absorbent articles.

Turing to FIG. 3 again, the waist containment member 54 can include at least one elastic member 86 located in the proximal portion 76 and, optionally, the distal portion 78. The elastic member 86 in the proximal portion 76 is designated proximal portion elastic member 86a and the elastic member 86 located in the distal portion 78 is designated distal portion elastic member 86b. It should be understood that in referencing the elastic members 86 (86a, 86b) that the singular term "member" is meant to include the plural "members" and vice versa in that an elastic member can comprise, for example, one elastic strand or multiple elastic strands or a single sheet of elastic material such as an elastic film.

The proximal portion elastic member 86a and the distal portion elastic member 86b can both extend in the lateral direction 32. They each can have a length in this regard and the proximal portion elastic member 86a can be less than, equal to or greater than the length of the distal portion elastic member 86b. In addition, the lengths of the elastic members 86 within either or both of the proximal portion 76 and the distal portion 78 can vary in length within the individual regions when multiple elastic members are being used. Either or both elastic members 86a, 86b can extend from the first longitudinal side edge 72 to the second longitudinal side edge 74. Alternatively, either or both elastic members 86a, 86b can extend a distance which is less than the width 51 of the waist containment member 54 as measured from the first longitudinal side edge 72 to the second longitudinal side edge 74 when the absorbent article 10 is in a stretched, laid-flat configuration. In an embodiment, the proximal portion elastic member 86a located in the proximal portion 76 can extend at least 70 percent of the distance between the first longitudinal side edge 72 and the second longitudinal side edge 74. In an embodiment, the proximal portion elastic member 86a located in the proximal portion 76 can extend at least 80 percent of the distance between the first longitudinal side edge 72 and the second longitudinal side edge 74. In an embodiment, the proximal portion elastic member 86a located in the proximal portion 76 can extend at least 90 percent of the distance between the first longitudinal side edge 72 and the second longitudinal side edge 74. Such percentages are determined when the absorbent article 10 is in a stretched, laid-flat configuration.

In an embodiment, the distal portion elastic member 86b located in the distal portion 78 can extend at least 70 percent of the distance between the first longitudinal side edge 72 and the second longitudinal side edge 74. In an embodiment, the distal portion elastic member 86b located in the distal portion 78 can extend at least 80 percent of the distance between the first longitudinal side edge 72 and the second longitudinal side edge 74. In an embodiment, the distal portion elastic member 86b located in the distal portion 78 can extend at least 90 percent of the distance between the first longitudinal side edge 72 and the second longitudinal side edge 74. Such percentages are determined when the absorbent article 10 is in a stretched, laid-flat configuration.

In still a further embodiment, one or more of the proximal portion elastic members 86a may be joined to one or more of the distal portion elastic members 86b, especially if the elastic members 86 are applied to the waist containment member 54 is a serpentine fashion.

Generally, it has been found advantageous for the length of the proximal portion elastic member 86a to be equal to the length of the distal portion elastic member 86b. However, in an embodiment, the length of the proximal portion elastic member 86a can be less than or greater than the length of the distal portion elastic member 86b. This length is determined when the absorbent article 10 is in a stretched, laid-flat configuration.

As shown in FIG. 3, the waist containment member 54 has a proximal end or edge 106 located in the proximal portion 76 and a distal end or edge 108 located in the distal portion 78. In some embodiments, such as the embodiment depicted in FIG. 3, the waist containment member 54 can include multiple elastic members 86, such as five distal portion elastic members 86b in the distal portion 78 and two proximal portion elastic members 86a in the proximal portion 76. Of course, it is contemplated that the waist containment member 54 can include other amounts of elastic members 86. In some embodiments, the elastic members 86 can be spaced evenly in the longitudinal direction 30 in either or both the proximal portion 76 and the distal portion 78 of the waist containment member 54. In some embodiments, the elastic members 86 can be spaced unevenly in the longitudinal direction 30 in either or both the proximal portion 76 and the distal portion 78 of the waist containment member 54.

The distal portion elastic member 86b can be disposed in the distal portion 78 of the waist containment member 54, and preferably, is located near the distal edge 108 of the distal portion 78 of the waist containment member 54. As illustrated in FIG. 3, in a preferred embodiment, the distal portion elastic member(s) 86b can be disposed within a laminate portion 90 of the distal portion 78 of the waist containment member 54 to aid in containing the distal portion elastic member(s) 86b. The laminate portion 90 can be disposed near the distal edge 108 of the distal portion 78 of the waist containment member 54. In some embodiments, the laminate portion 90 can be formed by a second fold 79b near the distal edge 108 of the distal portion 78. For example, in FIG. 3, the laminate portion 90 can be formed by a second fold 79b in the distal portion 78 at the distal edge 108 of the waist containment member 54. The tack-down regions 84 such as is show in FIG. 4, if present, can help retain the elastic member(s) 86 (86a, 86b) in place at the longitudinal side edges 72, 74, as well as help retain distal edge 108 in place.

In the embodiment shown in FIG. 3, the proximal portion 76 has its proximal portion elastic member 86a located on the second surface 104 of the waist containment material 101 of the waist containment member 54. To further isolate the elastic gathering effect from the body-contacting surface (first surface 102), a third fold 110 can be formed in the waist containment material 101 located in the proximal portion 76 of the waist containment member 54. As a result of this third fold 110, the proximal edge 106 is located closer to the crotch region 16 and the lateral axis 31 than is the first end edge 103. Conversely, the first end edge 103 of the waist containment material 101 is located closer to the rear waist edge 24 than is the proximal edge 106. As a result of this third fold 110, the proximal portion elastic members 86a are sandwiched between two layers of waist containment material 101 as a portion of the waist containment material 101 between the third fold 110 and the first end edge 103 is located in the vertical direction 100 above at least a portion of the proximal portion elastic member 86a in the proximal portion 76 of the waist containment member 54. Further, the proximal portion elastic member 86a may be coupled to the second surface 104 of the waist containment material 101 with adhesives or other means in the same fashion the distal portion elastic member 86b is adhered to the second surface 104 in the formation of the laminate portion 90.

In an alternate embodiment (not shown) the proximal portion elastic member 86a may be relocated to first surface 102 such that it is located in the area of the coupling adhesive 80 between the body facing surface of the chassis 11 (the body facing surface 45 of the absorbent assembly 44 or the body facing surface 56 of the body facing layer 28) and the first surface 102 of the proximal portion 76. In this embodiment, the third fold 110 may be maintained (and optionally coupled to the lower layer of material 101 in the proximal portion 76) or the portion of the waist containment material 101 between the third fold 110 and the first end edge 103 may be eliminated in which case the first end edge 103 will be coterminous with the proximal edge 106. The same is also true with respect to the waist containment material 101 in the distal portion 78 between the second fold 79b and the second end edge 105.

A wide variety of elastic materials may be used for the elastic member(s) 86 (86a, 86b) in the waist containment member 54. Suitable elastic materials can include sheets, strands or ribbons of natural rubber, synthetic rubber, thermoplastic elastomeric materials, or elastic foams. The elastic materials can be stretched and secured to a substrate forming the waist containment member 54, secured to a gathered substrate, or secured to a substrate and then elasticized or shrunk, for example, with the application of heat, such that the elastic retractive forces are imparted to the substrate forming the waist containment member 54.

As depicted in FIGS. 2 and 11, in some embodiments the waist containment member 54 can be disposed on the body facing surface 19 of the chassis 11 such that a gap 85 is provided between the second end edge 42 of the absorbent body 34 and the distal edge 108 of the distal portion 78 of the waist containment member 54. By providing a gap 85, the containment pocket 82 can have a greater void volume for body exudates. Additionally, it is believed that gap 85 can help body exudates enter the containment pocket 82 of the waist containment member 54.

The waist containment member 54 can be disposed to be coupled to the chassis 11 by being placed either over the containment flaps 50, 52 or under the containment flaps 50, 52. More specifically, as shown in FIGS. 2 and 11, the waist containment member 54 can be disposed on the body facing surface 19 of the chassis 11 such that the proximal portion 76 of the waist containment member 54 is disposed over the base portion 64 of the first and the second containment flaps 50, 52, respectively. Alternatively, the waist containment member 54 can be disposed on the body facing surface 19 of the chassis 11 such that the proximal portion 76 of the waist containment member 54 is disposed under the base portion 64 of the first and the second containment flaps 50, 52, respectively. Both configurations can provide advantages to the functioning of the waist containment member 54 to contain and/or absorb body exudates.

Embodiments where the proximal portion 76 of the waist containment member 54 is disposed over the base portion 64 of the containment flaps 50, 52 can provide the advantage that the containment flaps 50, 52 can help the distal portion 78 of the waist containment member 54 extend away from the body facing surface 45 of the absorbent assembly 44 when the absorbent article 10, 310 is applied to the wearer. This is especially relevant where the proximal portion 76 of the waist containment member 54 has a shorter longitudinal length than the distal portion 78 of the waist containment member 54. For example, because the proximal portion 76 is shorter than the distal portion 78, the flap elastics 68 in the projection portion 66 of the containment flaps 50, 52 can provide an opening force on the distal portion 78 of the waist containment member 54 when the absorbent article 10 is in the relaxed configuration and applied to the wearer, thus helping the distal portion 78 extend away from the body facing surface 45 of the absorbent assembly 44 and opening the containment pocket 82. In some embodiments, the containment pocket 82 can be additionally or alternatively opened by configuring the containment flaps 50, 52 to have an active flap elastic region 70 that longitudinally overlaps with the distal portion 78 of the waist containment member 54 when the absorbent article 10 is in the stretched, laid flat configuration, such as illustrated in FIG. 2. Additionally or alternatively, the containment pocket 82 of the waist containment member 54 can be opened by configuring the containment flaps 50, 52 to have a tack-down region 71 that does not extend to the distal edge 108 of the distal portion 78 of the waist containment member 54, such as illustrated in FIG. 2. However, such a configuration of the tack-down region 71 is not required, and in some embodiments, the tack-down region 71 can extend from the rear waist edge 24 past the distal edge 108 of the distal portion 78 of the waist containment member 54.

Embodiments where the proximal portion 76 of the waist containment member 54 is disposed under the base portion 64 of the containment flaps 50, 52 can provide the advantage of having the containment pocket 82 formed by the waist containment member 54 be free from the projection portion 66 of the containment flaps 50, 52. Both the base portion 64 and the projection portion 66 of each containment flap 50, 52 can be coupled to the body facing surface 55 of the waist containment member 54. As a result, body exudates may more freely spread through the full width of the containment pocket 82 created by the waist containment member 54. Additionally, the coupling of the base portion 64 of the containment flaps 50, 52 to the outer cover 26 (or in some embodiments to the bodyside liner 28) can create a longitudinal barrier to the flow of body exudates out of the containment pocket 82 for exudates that spread laterally beyond the location of the barrier adhesive 49. In some embodiments, the tack-down region 71 of the projection portion 66 of each of the containment flaps 50, 52 can longitudinally overlap with the distal portion 78 of the waist containment member 54. In some embodiments, the tack-down region 71 of projection portion 66 of each of the containment flaps 50, 52 can extend to the distal edge 108 of the waist containment member 54 to further assist in containing exudates within the containment pocket 82 created by the waist containment member 54.

Figure 5:
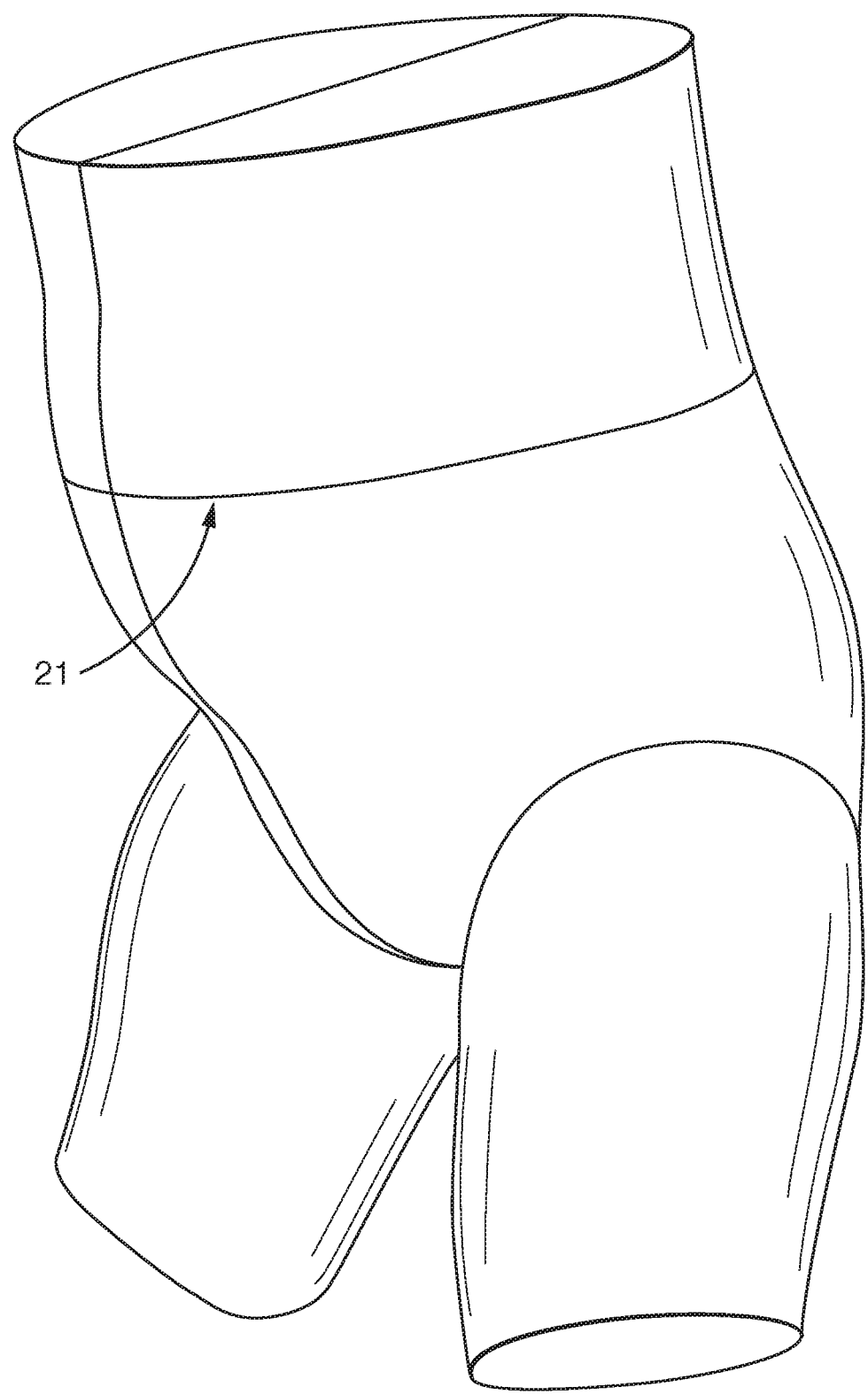
FIG. 5 is a perspective view of a torso of a wearer.
Figure 6:
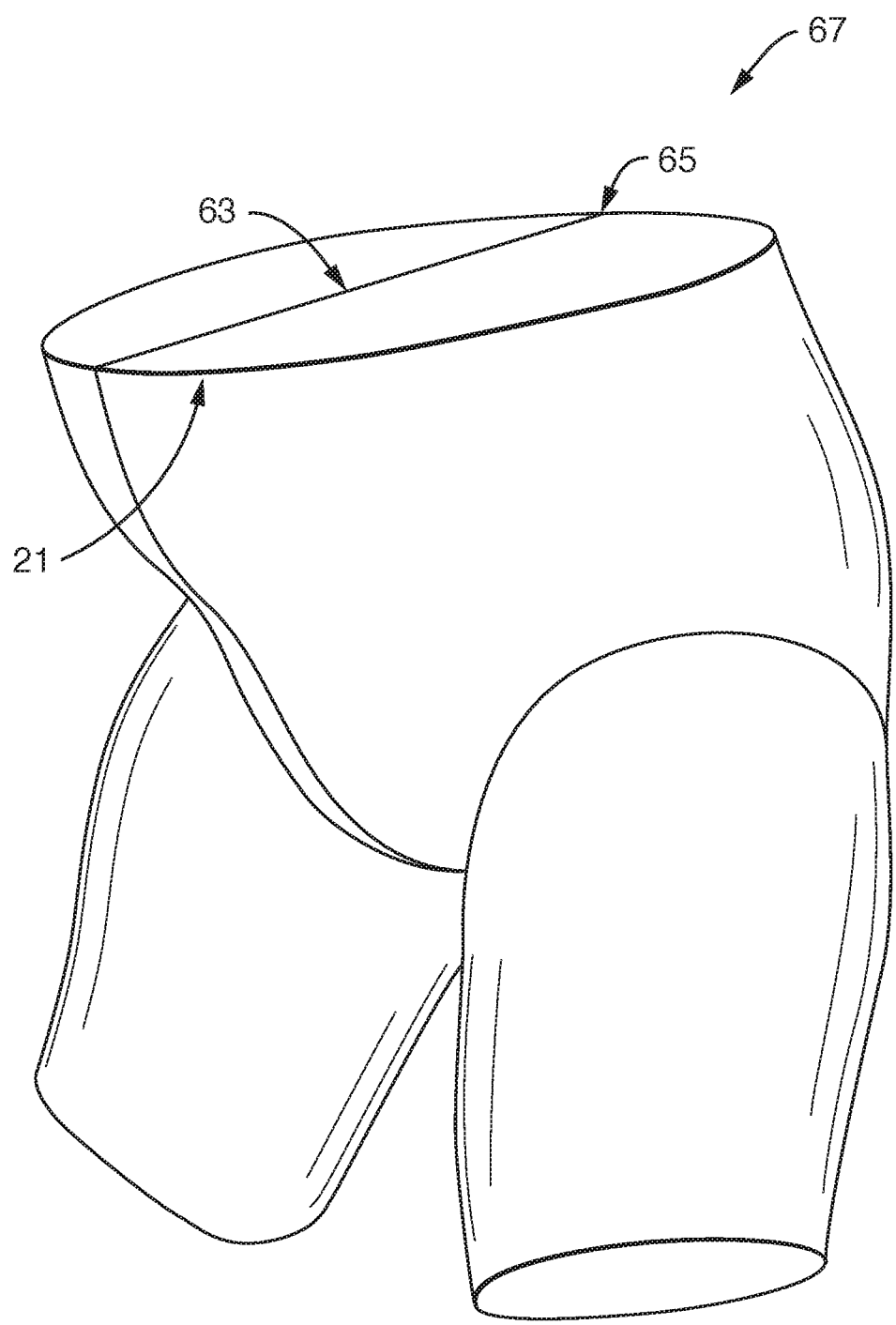
FIG. 6 is a perspective view of a torso of FIG. 5, with a cross-section taken at the waistline.

Turning to FIGS. 5-9, a series of anthropometric studies and data provide further understanding for why the addition of proximal portion elastic members 86a to the proximal portion 76 and the selective location of the distal edge 108 of the distal portion 78 of the waist containment member 54 can provide the benefit of reducing body exudates leaking from the absorbent article 10, 310. FIG. 5 depicts a digitized torso of a wearer, representative of an infant that is in the mid-range of a step 2 size diaper, approximately 15.7 pounds and 10 months old. The approximate waistline position 21 for where the front waist edge 22 and rear waist edge 24 would be located for a properly fitted absorbent article 10, 310 is shown. FIG. 6 provides a perspective view of the digitized torso of FIG. 5, with a cross-section taken at the waistline 21. FIG. 6 shows a bisection line 63 that bisects the torso. Point 65 is located where the bisection line 63 intersects the waistline 21 in the small of the back region 67 of the torso.

FIG. 7 provides a top plan view of the torso from FIG. 6 and shows point 65 at the intersection of the bisection line 63 with the waistline 21 in the small of the back region 67 of the wearer. As illustrated in FIG. 7, the small of the back region 67 at this location on the wearer's torso has a convex configuration. Two lines 63a and 63b are shown as being parallel to bisection line 63. Lines 63a and 63b are each spaced 25.0 mm, respectively, on opposite sides of the bisection line 63 and define the width of the small of the back region 67. The lines 63a and 63b intersect the waistline 21 of the torso at points 65a and 65b, respectively. A profile 77a of the back region of the torso of FIG. 5 is thus defined between points 65a and 65b, passing through point 65.

FIGS. 8A-8D provides profiles 77a, 77b, 77c, 77d of the back region of the torso from FIG. 5 at various cross-sections of the torso relative to the waistline 21, extending between points 65a and 65b discussed above. FIG. 8A provides the profile 77a of the back region of the torso of FIG. 5 at the cross-section taken right at the waistline 21. FIG. 8B provides a profile 77b of the back region of the torso taken 25.0 mm below the waistline 21. FIG. 8C provides a profile 77c of the back region of the torso taken 50.0 mm below the waistline 21. FIG. 8D provides a profile 77d of the back region of the torso taken 75.0 mm below the waistline 21. FIGS. 8A-8D depict how the torso transitions from a generally linear or slightly convex shape to a concave shape.

Viewing FIGS. 8A and 8B, it can be seen that the torso in the back region has a generally linear, or slightly convex profile 77a, 77b when viewed at the waistline 21 (FIG. 8A) and 25.0 mm below the waistline 21 (FIG. 8B). However, a concave nature in the profiles 77c and 77d in the back region of the torso can be seen when the torso is viewed at 50.0 mm below the waistline 21 (FIG. 8C) and 75.0 mm below the waistline 21 (FIG. 8D). The concave nature of the torso along profiles 77c and 77d depicts the gluteal depression on the torso. The gluteal depression provides a passage for body exudates to escape from an absorbent article, possibly soiling the wearer's back, clothing, sheets, or that of a caregiver. The depth of the gluteal depression at point 65 can be measured using modeling techniques for this torso, as well as other torsos.

Table 1 below shows the values of the depth of the gluteal depression for three representative wearer torsos as the distance from the waistline 21 increases. For example, the "Step 2 Girl" is the wearer's torso as illustrated in FIGS. 5-7 and shown in profiles 8A-8D and discussed above. The "Step 4 Girl" is of a 5th percentile for the step 4 size diaper, approximately 23.5 pounds. The "Step 4 Boy" is of a 75th percentile for the step 4 size diaper, approximately 34.4 pounds. Referring to Table 1 below, a negative value for the gluteal depression means that the profile including point 65 where the bisection line 63 intersects the small of the back region 67 is convex, such as discussed above and illustrated in FIG. 8A. Positive values for gluteal depression means that the profile including point 65 where the bisection line 63 intersects the small of the back region 67 is concave, such as discussed above and illustrated in FIGS. 8C and 8D.

TABLE 1

| Distance from | Depth of Gluteal Depression (mm) | | |
|---|---|---|---|
| diaper line (mm) | Step 2 Girl | Step 4 Girl | Step 4 Boy |
| 0 | −0.16 | −0.87 | −3.31 |
| 5 | −0.62 | −1.56 | −3.38 |
| 10 | −0.52 | −1.43 | −3.31 |

TABLE 1-continued

| Distance from diaper line (mm) | Depth of Gluteal Depression (mm) | | |
|---|---|---|---|
| | Step 2 Girl | Step 4 Girl | Step 4 Boy |
| 15 | −0.08 | −2.28 | −2.59 |
| 20 | −0.25 | −1.75 | −2.08 |
| 25 | −0.26 | −1.65 | −0.48 |
| 30 | 0.10 | −1.60 | 1.14 |
| 35 | 0.20 | −1.21 | 2.79 |
| 40 | 0.02 | −0.71 | 5.18 |
| 45 | 0.33 | 0.76 | 7.17 |
| 50 | 0.54 | 2.68 | 8.35 |
| 55 | 1.17 | 5.89 | 9.60 |
| 60 | 2.49 | 6.95 | 10.17 |
| 65 | 3.04 | 8.35 | 10.33 |
| 70 | 3.41 | 9.05 | 10.24 |
| 75 | 3.37 | 9.34 | 9.55 |
| 80 | 3.66 | 10.06 | 9.55 |

Figure 9:
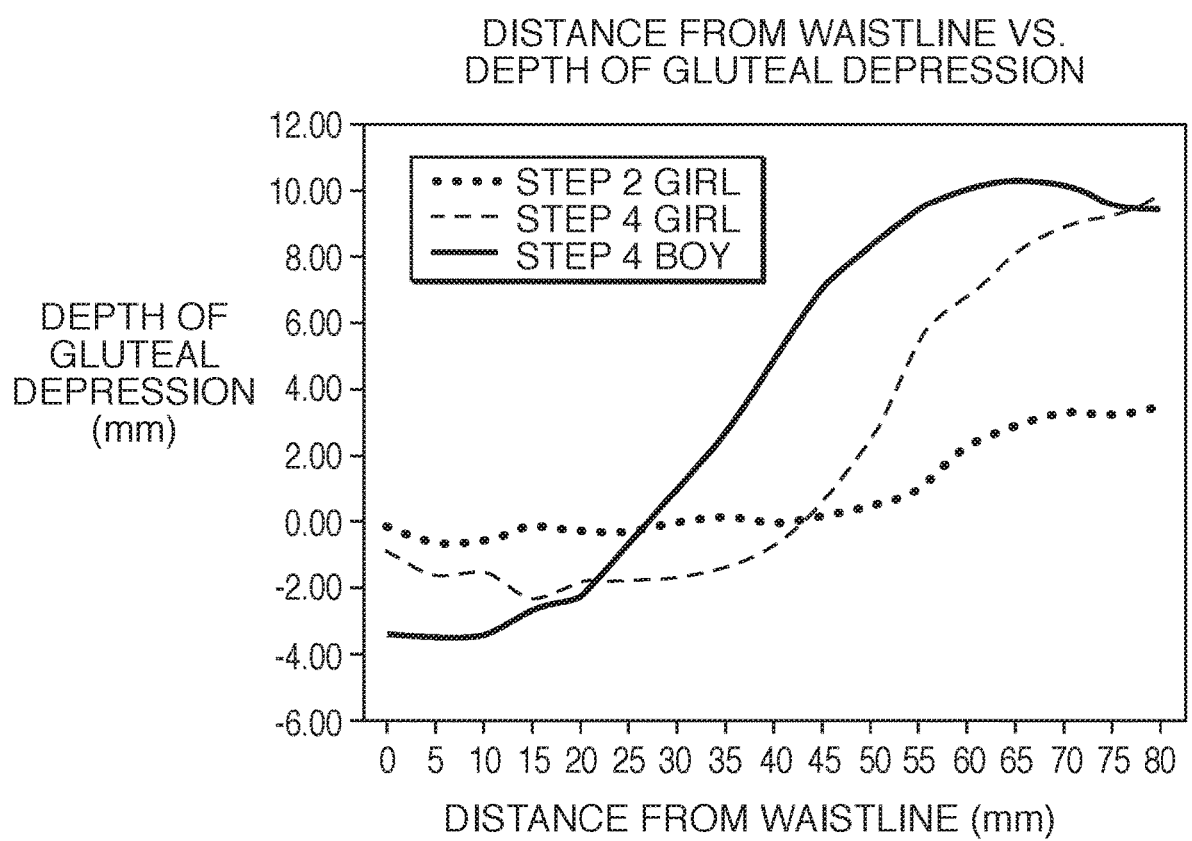
FIG. 9 is a graph depicting the distance from waistline vs. depth of gluteal depression values from Table 1.

FIG. 9 provides a graphical illustration for the depth of the gluteal depression values from Table 1. As illustrated in FIG. 9, it is apparent that for at least the representative samples analyzed for Step 2 Girl, Step 4 Girl, and Step 4 Boy, the depth of the gluteal depression increases at a greater rate once the distance from the diaper line reaches about 30.0 mm to about 50.0 mm below the waistline 21. Based on this anthropometric analysis, in some embodiments it can be preferable to have the proximal portion 76 of the waist containment member 54 and the included proximal portion elastic member 86a closer to rear waist edge 24 when the waist containment member is located in the rear waist region 14 and/or closer to the front waist edge 22 when a waist containment member 54 is located in the front waist region 12. In this regard, the first fold 79a can be positioned such that it is less than 40 millimeters (mm) from the respective rear waist edge 24 and/or front waist edge 22 depending on whether one or two waist containment members 54 are being used and whether they are in the front and/or rear waist regions 12, 14. More preferably, the first fold 79a can be positioned such that it is less than 15 millimeters mm from the respective rear waist edge 24 and/or front waist edge 22 depending on whether one or two waist containment members 54 are being used and whether they are in the front and/or rear waist regions 12, 14. Even more preferably, the first fold 79a can be positioned such that it is less than 1 mm from or at the respective rear waist edge 24 and/or front waist edge 22 depending on whether one or two waist containment members 54 are being used and whether they are in the front and/or rear waist regions 12, 14.

The location and functionality of the first fold 79a and thus the proximal portion 76 of the waist containment member 54 can be further enhance when the distal edge 108 of the distal portion 78 is from about 60 to about 40 mm from the rear waist edge 24 of the absorbent article 10, especially for absorbent articles 10 that are configured as diapers and intended to be worn by young children. More preferably, the distal edge 108 of the distal portion 78 is from about 55 to about 45 mm from the rear waist edge 24 of the absorbent article 10. This same spacing can be used when the waist containment member 54 is located in the front waist region 12 of the absorbent article 10. Configuring the waist containment member 54 in such a fashion can provide better contact of the first surface 102 of the waist containment member 54 with the small of the back of the wearer as well as the distal edge 108 of the distal portion 78 of the waist containment member 54 against the wearer's skin along the entire width 51 of the waist containment member 54 and thus, reduce the possibility of body exudates escaping from the absorbent article 10, 310. Of course, it is contemplated that the distal edge 108 of the distal portion 78 can be more than about 60 mm from the rear waist edge 24 of the absorbent article 10 and still be within the scope of this disclosure. It can also be appreciated that a wearer's profile in the back region can vary from individual to individual, as well as from different age classes of individuals. For purposes herein, the measurement of the distal edge 108 of the distal portion 78 of the waist containment member 54 to the rear waist edge 24 of the absorbent article 10, 310 is to be measured when the absorbent article 10, 310 is in the stretched, laid-flat configuration.

The waist containment material 101 used to form the waist containment member 54 can be comprised of a variety of materials. In a preferred embodiment, the waist containment material 101 forming the waist containment member 54 can be comprised of a spunbond-meltblown-spunbond ("SMS") material. However it is contemplated that the waist containment material 101 and thus the waist containment member 54 can be comprised of other materials including, but not limited to, a spunbond-film-spunbond ("SFS"), a bonded carded web ("BCW"), or any non-woven material. In some embodiments, the waist containment member 54 can be comprised of a laminate of more than one of these exemplary materials, or other materials. In some embodiments, the waist containment member 54 can be comprised of a liquid impermeable material such as a film or a film/nonwoven laminate. In some embodiments the film may be breathable such as a microporous film or a film that has been apertured. In some embodiments, the waist containment member 54 can be comprised of a material coated with a hydrophobic coating. The basis weight of the material forming the waist containment member 54 can vary, however, in a preferred embodiment, the basis weight can be between about 8 gsm to about 120 gsm, not including the elastic members 86 in the waist containment member 54. More preferably, the basis weight of the material comprising the waist containment member 54 can be between about 10 gsm to about 40 gsm, and even more preferably, between about 15 gsm to about 25 gsm.

The relative spacing of the components of the absorbent article 10, 310 can be configured in a number of ways to achieve the desired attributes of the present invention. In an embodiment, the first fold 79a of the waist containment member 54 can be closer than the proximal portion elastic member 86a of the same waist containment member 54 to the respective front waist edge 22 or the rear waist edge 24 to which the proximal portion 76 of the waist containment member 54 is more closely coupled when the absorbent article 10, 310 is in a stretched, laid flat configuration. In an embodiment, the distal edge 108 of the distal portion 78 of the waist containment member 54 can be closer to the lateral axis 31 and the crotch region 16 than the first fold 79a of the proximal portion 76 when the absorbent article 10, 310 is in a stretched, laid flat configuration. In an embodiment, the proximal portion elastic member 86a in the proximal portion 76 of the waist containment member 54 can be located closer to the lateral axis 31 and the crotch region 16 than the first fold 79a when the absorbent article 10, 310 is in a stretched, laid flat configuration. In an embodiment, the proximal edge 106 of the proximal portion 76 of the waist containment member 54 is closer to the lateral axis 31 and the crotch region 16 than the first fold 79a when the absorbent article 10, 310 is in a stretched, laid flat configuration. In an embodiment, the second fold 79b of the distal portion 78 of the waist containment member 54 is closer to the lateral axis 31 and the crotch region 16 than the distal portion elastic member 86*b* in the distal portion 78 when the absorbent article 10, 310 is in a stretched, laid flat configuration.

Fastening System:

In an embodiment, the absorbent article 10, can include a fastening system. The fastening system can include one or more back fasteners 91 and one or more front fasteners 92. The embodiments being shown in FIGS. 1 and 2 depict embodiments with one front fastener 92. Portions of the fastening system may be included in the front waist region 12, rear waist region 14, or both.

The fastening system can be configured to secure the absorbent article 10 about the waist of the wearer in a fastened condition as shown in FIG. 1 and help maintain the absorbent article 10 in place during use. In an embodiment, the back fasteners 91 can include one or more materials bonded together to form a composite ear as is known in the art. For example, the composite fastener may be composed of a stretch component 94, a nonwoven carrier or hook base 96, and a fastening component 98, as labeled in FIG. 2. In some embodiments the waist containment member 54 can laterally extend to the back fasteners 91, and/or to each of the longitudinal side edges 18, 20 of the absorbent article 10, 310. In some embodiments, the waist containment member 54 can be coupled to the stretch component 94 of the back fasteners 91, either directly or indirectly.

EMBODIMENTS

Embodiment 1

An absorbent article including a front waist region including a front waist edge, a rear waist region including a rear waist edge, a crotch region disposed intermediate the front waist edge and the rear waist edge, the absorbent article defining a longitudinal axis, a lateral axis located midway between the front waist edge and the rear waist edge and a vertical axis, the absorbent article comprising:
  a chassis including an absorbent body, the chassis including a body facing surface; and
  a waist containment member disposed on the body facing surface of the chassis, the waist containment member comprising:
  a waist containment material having a first longitudinal side edge and a second longitudinal side edge, a first end edge and a second end edge;
  the waist containment member having a proximal portion with a proximal edge and including a proximal portion elastic member, the proximal portion being coupled to the body facing surface of the chassis adjacent the front waist edge or the rear waist edge; and
  the waist containment member having a distal portion with a distal edge;
  the waist containment material having a first fold extending in the direction of the lateral axis, the first fold being closer than the proximal portion elastic member to the respective front waist edge or rear waist edge to which the proximal portion is more closely coupled when the absorbent article is in a stretched, laid flat configuration;
  the distal edge being closer to lateral axis than the first fold and the distal portion being free to move with respect to the chassis when the absorbent article is in a relaxed configuration so as to form a pocket with the chassis.

Embodiment 2

The absorbent article of embodiment 1 wherein the distal portion includes a distal portion elastic member located in the distal portion.

Embodiment 3

The absorbent article of embodiment 2 wherein the proximal portion elastic member in the proximal portion comprises a plurality or elastic strands.

Embodiment 4

The absorbent article of embodiment 3 wherein the distal portion elastic member in the distal portion comprises a plurality of elastic strands.

Embodiment 5

The absorbent article of embodiment 4 wherein there is a lesser number of the elastic strands in the proximal portion than the elastic strands in the distal portion.

Embodiment 6

The absorbent article of embodiment 1 wherein the waist containment material has a first surface and a second surface, and the first surface is coupled to the chassis.

Embodiment 7

The absorbent article of embodiment 6 wherein the proximal portion elastic member in the proximal portion is located between the first surface and the chassis and the proximal portion elastic member in the proximal portion is closer to the lateral axis than is the first fold when the absorbent article is in a stretched, laid flat configuration.

Embodiment 8

The absorbent article of embodiment 6 wherein the proximal portion elastic member in the proximal portion is attached to the second surface of the waist containment material and the proximal portion elastic member in the proximal portion is closer to the lateral axis than is the first fold when the absorbent article is in a stretched, laid flat configuration.

Embodiment 9

The absorbent article of embodiment 7 wherein the proximal edge is closer to the lateral axis than is the first fold when the absorbent article is in a stretched, laid flat configuration.

Embodiment 10

The absorbent article of embodiment 8 wherein the proximal edge is closer to the lateral axis than is the first fold when the absorbent article is in a stretched, laid flat configuration.

Embodiment 11

The absorbent article of embodiment 1 wherein the waist containment material has a second fold extending in the direction of the lateral axis, the second fold being located in the distal portion.

Embodiment 12

The absorbent article of embodiment 11 wherein the waist containment material has a first surface and a second surface, and the first surface is coupled to the chassis, and wherein a distal portion elastic member is located in the distal portion and is attached to the second surface of the containment material and the second fold is closer to the lateral axis than is the distal portion elastic member in the distal portion when the absorbent article is in a stretched, laid flat configuration.

Embodiment 13

The absorbent article of embodiment 12 wherein the chassis further comprises a bodyside liner and an outer cover, the bodyside liner having a body facing surface, the absorbent body being disposed between the bodyside liner and the outer cover and wherein the proximal portion of the waist containment member is coupled to the body facing surface of the bodyside liner.

Embodiment 14

The absorbent article of embodiment 13 wherein the distal portion elastic member located in the distal portion extends at least 70 percent of a distance from the first longitudinal side edge to the second longitudinal side edge of the waist containment member when the absorbent article is in a stretched, laid flat configuration.

Embodiment 15

The absorbent article of embodiment 14 wherein the proximal portion elastic member located in the proximal portion extends at least 70 percent of a distance from the first longitudinal side edge to the second longitudinal side edge of the waist containment member when the absorbent article is in a stretched, laid flat configuration.

Embodiment 16

The absorbent article of embodiment 11 wherein the waist containment material has a third fold in the proximal portion whereby a portion of the waist containment material between the third fold and the first end edge is located in the direction of the vertical axis above at least a portion of the proximal portion elastic member in the proximal portion of the waist containment member when the absorbent article is in a stretched, laid flat configuration.

Embodiment 17

The absorbent article of embodiment 16 wherein the third fold forms the proximal edge of the containment member.

Embodiment 18

An absorbent article including a front waist region including a front waist edge, a rear waist region including a rear waist edge, a crotch region disposed intermediate the front waist edge and the rear waist edge, the absorbent article defining a longitudinal axis, a lateral axis located midway between the front waist edge and the rear waist edge and a vertical axis, the absorbent article comprising:
- a chassis including an absorbent body, the chassis including a body facing surface; and
- a waist containment member disposed on the body facing surface of the chassis, the waist containment member having a first longitudinal side edge and a second longitudinal side edge, a first end edge and a second end edge;
- the waist containment member having a proximal portion with a proximal edge defining a proximal portion lateral width between the first longitudinal side edge and the second longitudinal side edge in the proximal portion, the waist containment member including a proximal portion elastic member, the proximal portion being coupled to the body facing surface of the chassis adjacent the front waist edge or the rear waist edge; and
- the waist containment member having a distal portion with a distal edge defining a distal portion lateral width between the first longitudinal side edge and the second longitudinal side edge in the distal portion; the proximal portion lateral width being equal to or greater than the distal portion lateral width when the absorbent article is in a stretched, laid flat configuration;
- the distal edge being free to move with respect to the chassis when the absorbent article is in a relaxed configuration so as to form a pocket with the chassis.

Embodiment 19

The absorbent article of embodiment 18 wherein the waist containment member has a first fold extending in the direction of the lateral axis, the first fold being closer than the proximal portion elastic member to the respective front waist edge or rear waist edge to which the proximal portion is more closely coupled when the absorbent article is in a stretched, laid flat configuration;
the distal edge being closer to the lateral axis than the first fold.

Embodiment 20

The absorbent article of embodiment 19 wherein the distal portion includes a distal portion elastic member located in the distal portion.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article including a front waist region including a front waist edge, a rear waist region including a rear waist edge, a crotch region disposed intermediate the front waist edge and the rear waist edge, the absorbent article defining a longitudinal axis, a lateral axis located midway between the front waist edge and the rear waist edge and a vertical axis, the absorbent article comprising:
- a chassis including an absorbent body, the chassis including a body facing surface; and
- a waist containment member being separate from the chassis and coupled to the body facing surface of the chassis, the waist containment member being an elastic laminate formed of a waist containment material and a plurality of elastic members, the waist containment member having a first longitudinal side edge and a second longitudinal side edge, a first end edge and a second end edge;
- the waist containment member having a proximal portion with a proximal edge defining a proximal portion lateral width between the first longitudinal side edge and the second longitudinal side edge in the proximal portion, the waist containment member including a proximal portion elastic member, the proximal portion being coupled to the body facing surface of the chassis adjacent the front waist edge or the rear waist edge; and
- the waist containment member having a distal portion with an outermost distal edge defining a distal portion lateral width between the first longitudinal side edge and the second longitudinal side edge in the distal portion, the proximal portion lateral width being equal to or greater than the distal portion lateral width when the absorbent article is in a stretched, laid flat configuration;
- the distal portion including a distal portion elastic member located in the distal portion with the distal edge being free to move with respect to the chassis when the absorbent article is in a relaxed configuration so as to form a pocket with the chassis,
- wherein the waist containment member has a first fold extending in the direction of the lateral axis when the absorbent article is in a stretched, laid flat configuration, the first fold defining a transition between the proximal portion and the distal portion, and
- wherein the first fold is closer than the proximal portion elastic member to the respective front waist edge or rear waist edge to which the proximal portion is more closely coupled, and where the distal edge is closer to the lateral axis than the first fold.

2. The absorbent article of claim 1, further comprising a first containment flap extending between the front waist region and the rear waist region and a second containment flap extending between the front waist region and the rear waist region, each of the first containment flap and the second containment flap comprising a base portion coupled to the body facing surface and a projection portion configured to extend away from the body facing surface.

3. The absorbent article of claim 2, wherein the waist containment member is coupled to the body facing surface of the chassis such that at least part of the projection portions of each of the first containment flap and the second containment flap are disposed between the waist containment member and the absorbent body.

4. The absorbent article of claim 3, wherein the waist containment member is coupled to the body facing surface of the chassis such that at least part of the base portions each of the first containment flap and the second containment flap are disposed between the waist containment member and the absorbent body.

5. The absorbent article of claim 3, wherein the waist containment member is coupled to the body facing surface of the chassis between the projections portions of the first containment flap and the second containment flap.

6. The absorbent article of claim 3, wherein at least a portion of the waist containment member is coupled to the first containment flap and the second containment flap.

7. The absorbent article of claim 1, wherein the distal portion is bonded to the proximal portion proximate at least one of the first longitudinal side edge and the second longitudinal side edge.

8. The absorbent article of claim 1, wherein the proximal portion lateral width is between about 10 percent and about 40 percent greater than the distal portion lateral width.

9. The absorbent article of claim 1, wherein the proximal portion lateral width is between about 20 percent and about 30 percent greater than the distal portion lateral width.

10. The absorbent article of claim 1, wherein the first longitudinal side edge and the second longitudinal side edge extend in a non-linear fashion.

11. The absorbent article of claim 1, wherein the proximal portion comprises a first material and the distal portion comprises a second, different material, the first material and the second material being bonded together.

12. The absorbent article of claim 1, wherein the distal portion includes a distal portion elastic member located in the distal portion.

13. The absorbent article of claim 1, wherein the proximal portion elastic member in the proximal portion comprises a plurality of elastic strands.

* * * * *